(12) United States Patent
Olson et al.

(10) Patent No.: US 11,166,949 B2
(45) Date of Patent: Nov. 9, 2021

(54) NURR1 ACTIVATION IN THE TREATMENT OF METABOLIC DISORDERS AND AS AN EXERCISE MIMETIC

(71) Applicant: The Board of Regents of the University of Texas System, Austin, TX (US)

(72) Inventors: Eric N. Olson, University Park, TX (US); Rhonda Bassel-Duby, Dallas, TX (US); Leonela Amoasii, Dallas, TX (US)

(73) Assignee: The Board of Regents of The University of Texas System, Austin, TX (US)

( * ) Notice: Subject to any disclaimer, the term of this patent is extended or adjusted under 35 U.S.C. 154(b) by 116 days.

(21) Appl. No.: 16/096,536

(22) PCT Filed: Apr. 26, 2017

(86) PCT No.: PCT/US2017/029575
§ 371 (c)(1),
(2) Date: Apr. 1, 2019

(87) PCT Pub. No.: WO2017/189686
PCT Pub. Date: Nov. 2, 2017

(65) Prior Publication Data
US 2019/0134021 A1  May 9, 2019

Related U.S. Application Data

(60) Provisional application No. 62/328,493, filed on Apr. 27, 2016.

(51) Int. Cl.
| | | |
|---|---|---|
| *A61K 31/47* | (2006.01) |
| *A61P 3/04* | (2006.01) |
| *A61K 31/4706* | (2006.01) |
| *A61K 38/28* | (2006.01) |
| *A61K 45/06* | (2006.01) |
| *A61K 31/437* | (2006.01) |
| *A61K 38/22* | (2006.01) |
| *A61P 1/16* | (2006.01) |

(52) U.S. Cl.
CPC ........ *A61K 31/4706* (2013.01); *A61K 31/437* (2013.01); *A61K 31/47* (2013.01); *A61K 38/2264* (2013.01); *A61K 38/28* (2013.01); *A61K 45/06* (2013.01); *A61P 1/16* (2018.01); *A61P 3/04* (2018.01)

(58) Field of Classification Search
CPC .................................. A61K 31/47; A61P 3/04
USPC ........................................................ 514/313
See application file for complete search history.

(56) References Cited

U.S. PATENT DOCUMENTS

| | | |
|---|---|---|
| 8,440,695 B2 | 5/2013 | Kastan et al. |
| 2013/0274212 A1 | 10/2013 | Kang et al. |
| 2014/0275164 A1 | 9/2014 | Robinson et al. |

FOREIGN PATENT DOCUMENTS

WO  WO 2016-133352  8/2016

OTHER PUBLICATIONS

Amoasii, et al, "A MED13-dependent: skeletal muscle gene program controls systemic glucose homeostasis and hepatic metabolism." *Genes & development* 30.4 (20.16): 434-446.
Catoire, et al. "Pronounced effects of acute endurance exercise on gene expression in resting and exercising human skeletal muscle." *PloS One* 7.11 (2012): e51066.
Chao, et al. "Nur77 coordinately regulates expression of genes linked to glucose metabolism in skeletal muscle." *Molecular Endocrinology* 21.9 (2007): 2152-2163.
De Miranda et al., "The Nurr1 Activator 1,1-Bis(3'-Indolyl)-1-(p-Chlorophenyl)Methane Blocks Inflammatory Gene Expression in BV-2 Microglial Cells by Inhibiting Nuclear Factor κB," *Molecular Pharmacology*, 87(6):1021-1034, 2015.
Fu, et al. "NR4A Orphan Nuclear Receptors Modulate Insulin Action and the Glucose Transport System Potential Role in Insulin Resistance." *Journal of Biological Chemistry* 282.43 (2007): 31525-31533.
Kim, et al. "Nuclear receptor Nurr1 agonists enhance its dual functions and improve behavioral deficits in an animal model of Parkinson's disease." *Proceedings of the National Academy of Sciences* 112.28 (2015): 8756-8761.
Myers, et al. "β-Adrenergic signaling regulates NR4A nuclear receptor and metabolic gene expression in multiple tissues." *Molecular and cellular endocrinology* 309.1-2 (2009): 101-108.
PCT International Preliminary Report on Patentability issued in International Application No. PCT/US2017/029575 dated Nov. 8, 2018.
PCT International Search Report and Written Opinion issued in International Application No. PCT/US2017/029575 dated Sep. 13, 2017.
Pearen, et al. "Minireview: Nuclear hormone receptor 4A signaling: implications for metabolic disease." *Molecular endocrinology* 24.10 (2010): 1891-1903.
Pearen, et al. "The nuclear receptor, Nor-1, markedly increases type II oxidative muscle fibers and resistance to fatigue." *Molecular Endocrinology* 26.3 (2012): 372-384.
Yoon, et al. "Activation of nuclear TR3 (NR4A1) by a diindolylmethane analog induces apoptosis and proapoptotic genes in pancreatic cancer cells and tumors." *Carcinogenesis* 32.6 (2011): 836-842.

*Primary Examiner* — Raymond J Henley, III
(74) *Attorney, Agent, or Firm* — Parker Highlander PLLC

(57) ABSTRACT

The present disclosure relates to the identification of Nurr1 as a key regulator of metabolism, and the use of Nurr1 agonist to treat metabolic disorders such as diabetes, obesity, metabolic syndrome and hepatic steatosis.

4 Claims, 19 Drawing Sheets

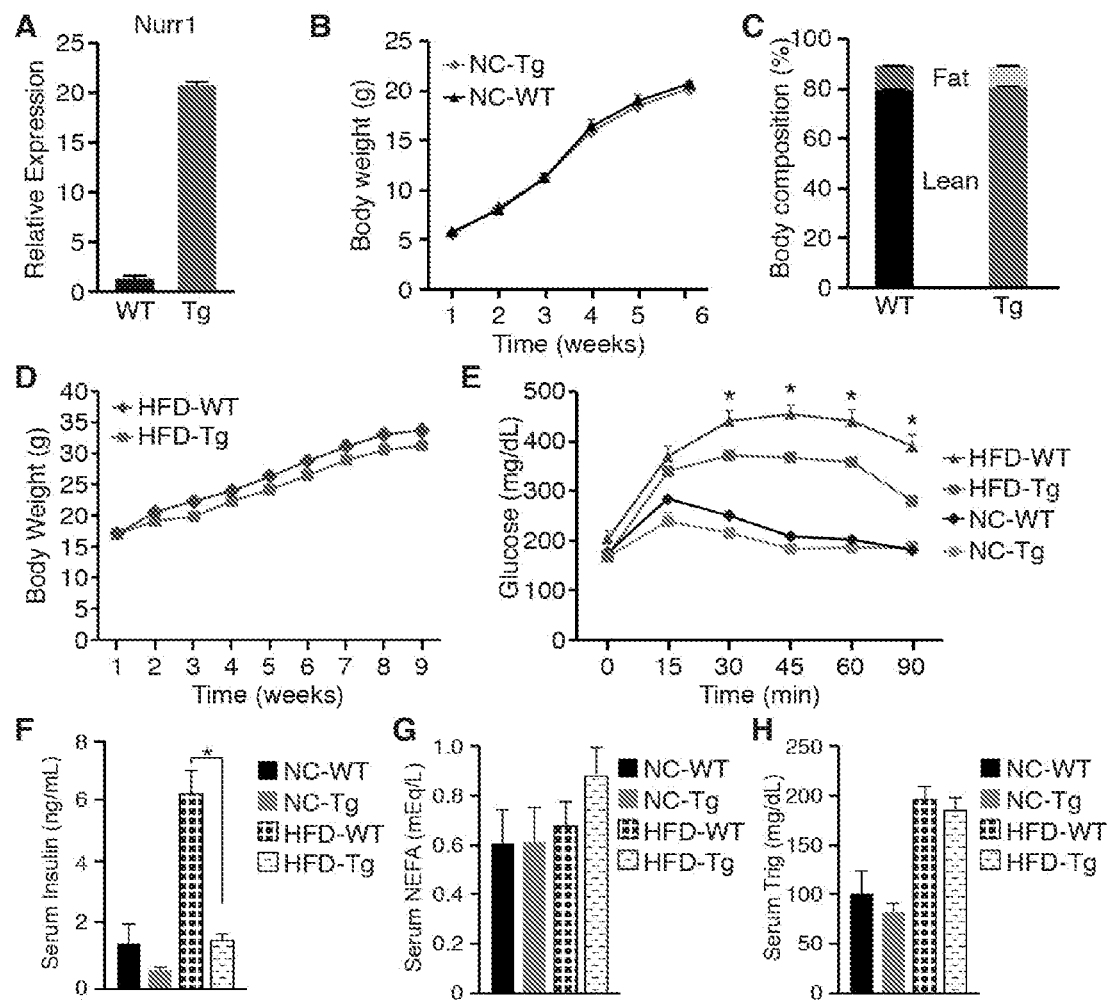
FIGS. 1A-H

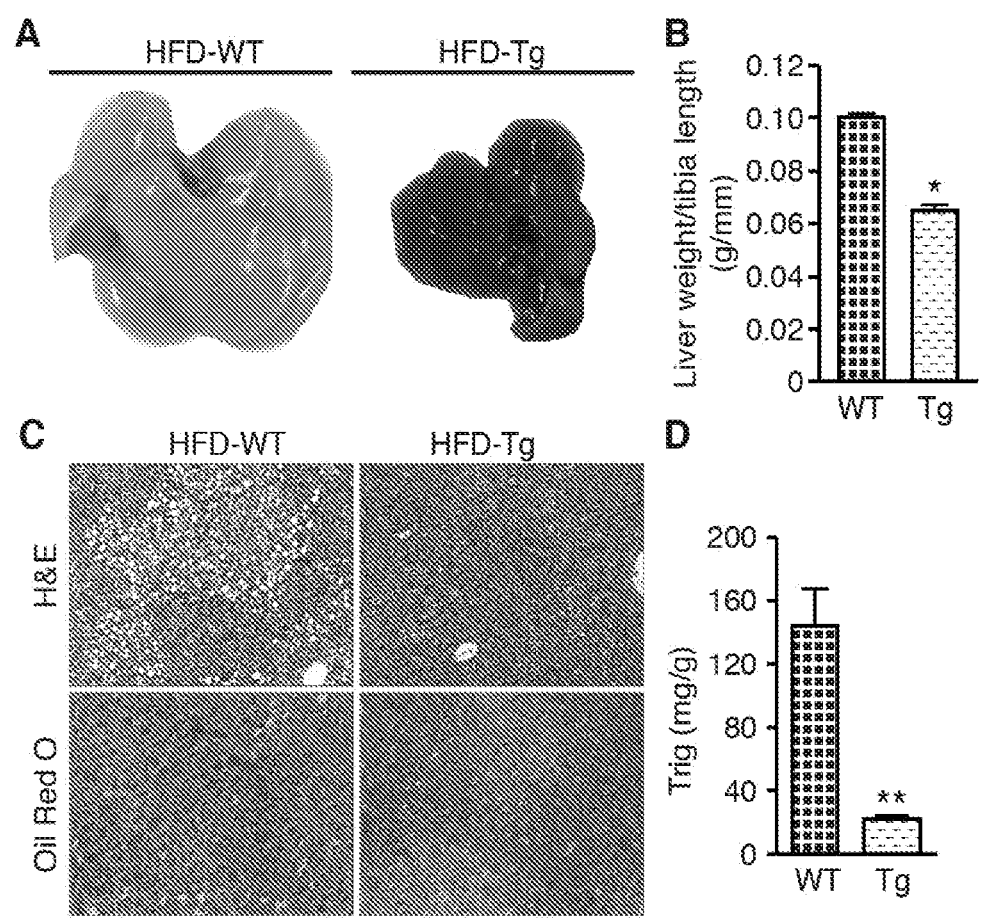
FIGS. 2A-D

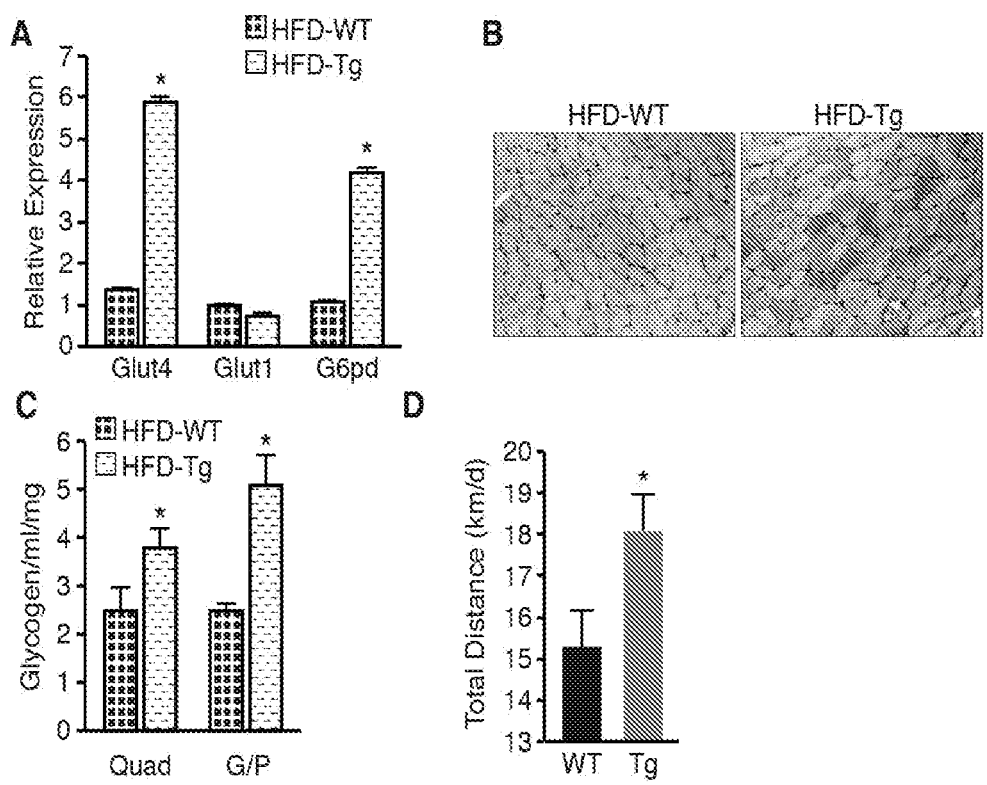
FIGS. 3A-D

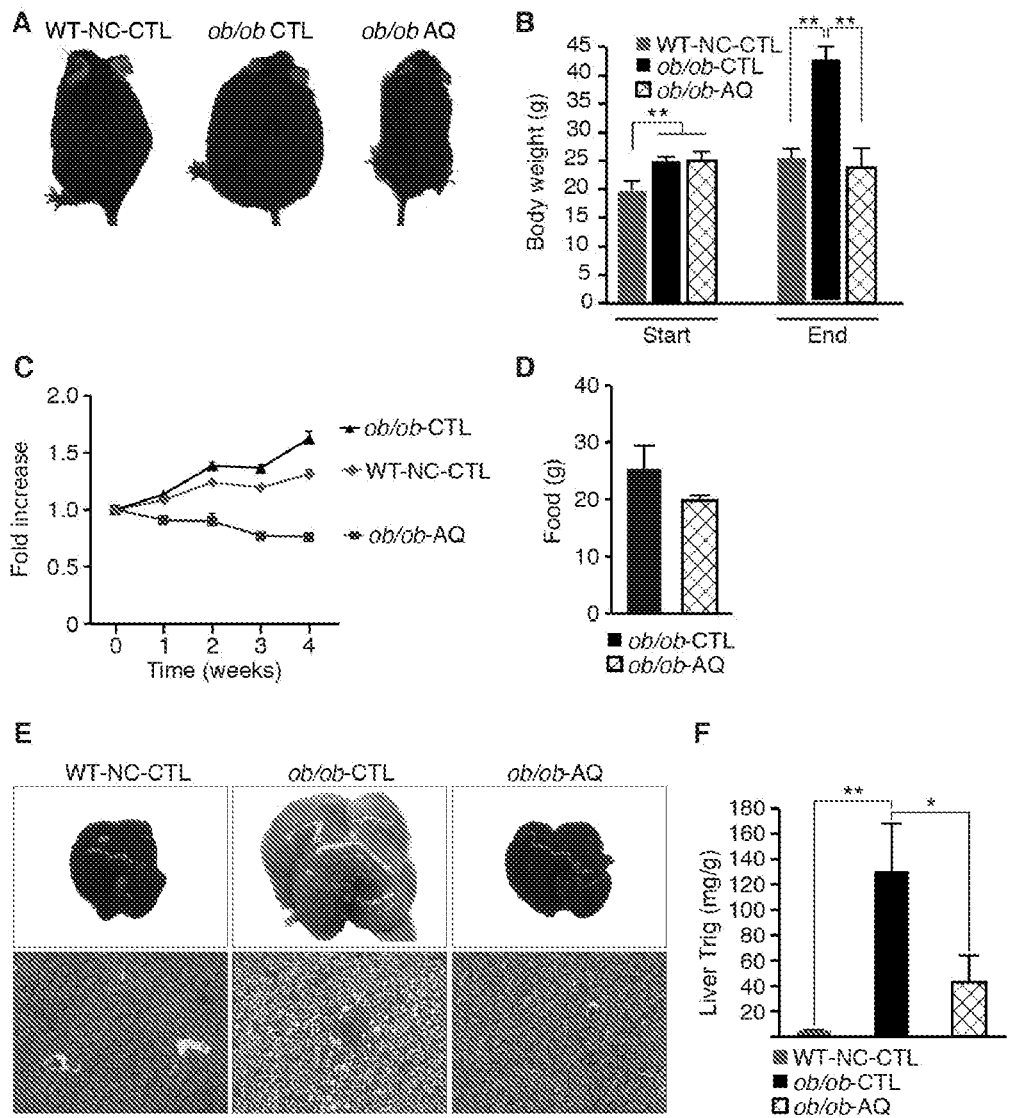
FIGS. 5A-F

NURR1 ACTIVATION IN THE TREATMENT OF METABOLIC DISORDERS AND AS AN EXERCISE MIMETIC

This application is a national phase application under 35 U.S.C. § 371 of International Application No. PCT/US2017/029575, filed Apr. 26, 2017, which claims benefit of priority to U.S. Provisional Application Ser. No. 62/328,493, filed Apr. 27, 2016, the entire contents of each of which are hereby incorporated by reference.

This invention was made with government support under grant number DK099653 awarded by The National Institutes of Health. The government has certain rights in the invention.

BACKGROUND

I. Technical Field

The present disclosure relates generally to the fields of medicine, metabolism and skeletal muscle physiology. More particularly, it relates to the targeting of the Nurr1 receptor for the treatment and prevention of hepatic steatosis, metabolic syndrome and to mimic the results of exercise.

II. Related Art

While the beneficial effects of exercise on metabolism and overall organismal health are well known, much remains to be learned about the mechanistic basis of the benefits of physical activity and the systemic interactions among tissues and organs. Skeletal muscle accounts for ~40% of body mass in healthy individuals and represents the major site of glucose uptake and metabolism in the body. During exercise, glycogen is broken down in the liver to provide glucose, which is taken up by skeletal muscle to provide energy for contraction. Conversely, under conditions of caloric excess, glucose and fatty acids are directed to the liver where they are stored as triglycerides, causing hepatic steatosis, a growing health concern.

Uptake of glucose by skeletal muscle is mediated by GLUT4, the major glucose transporter in the sarcolemma (Richter and Hargreaves, 2013). Exercise induces the expression and translocation of GLUT4 from intracellular stores to the sarcolemma and activates a variety of signal transduction pathways that culminate in the nucleus to modulate the expression of GLUT4 and other metabolic genes (M Lehnen, 2013). Key among the exercise-responsive signaling pathways are AMPK and several calcium-sensitive kinases that regulate transcription by targeting class II HDACs. Phosphorylation of class II HDACs promotes their export from the nucleus to the cytoplasm, relieving their repressive influence on MEF2 and other transcription factors (Potthoff and Olson, 2007). Integration of metabolic gene regulation also occurs through regulatory interactions between MEF2 and the nuclear coactivator PGC1, which associates with PPAR and other nuclear receptors to enhance metabolic gene expression (Lin et al., 2002).

Recently, the inventors showed that MED13, a component of the Mediator complex, acts in skeletal muscle to modulate systemic metabolism by suppressing the expression of GLUT4 and other genes involved in glucose uptake and glycogen storage (Amoasii et al., 2016). Thus, mice with muscle-specific deletion of MED13 showed enhanced muscle glucose uptake and resistance to hepatic steatosis due to diversion of energy away from the liver and uptake into muscle under conditions of caloric excess. Among a collection of genes up-regulated in skeletal muscle was the orphan nuclear receptor NR4A2, also known as Nurr1. Over-expression of Nurr1 in C2C12 myotubes in culture enhanced glucose uptake and expression of GLUT4. Nurr1 has been implicated in survival of dopaminergic neurons, as well as a variety of processes. Intriguingly, drug screen study identified a collection of compounds sharing a common chemical scaffold with a bis (3'-indolyl) moiety that are capable of activating Nurr1 by binding the ligand-binding domain (Kim et al., 2015). These compounds have been shown to display anti-malarial activity and to show beneficial effects in Parkinson's Disease by enhancing dopamine neurotransmission and also protecting dopaminergic neurons from injury induced by environmental toxin or microglia-mediated neuroinflammation (Kim et al., 2015). Even though Nurr1 role and its beneficial impact have been studied for Parkinson's disease in vivo, but its potential involvement in skeletal metabolism in vivo has not been previously investigated.

SUMMARY

Thus, in accordance with the present disclosure, there is provided a method for preventing or treating hepatic steatosis comprising administering to a subject in need thereof a Nurr1 agonist, or a method of increasing endurance and/or athletic performance comprising administering to a subject in need thereof a Nurr1 agonist. The Nurr1 agonist may be a bis (3'-indolyl)-containing molecule, a 1,1-bis(3'-indolyl)-1-(p-substituted phenyl)methane compound, amodiaquine or a derivative or analog thereof. The subject may be obese or overweight, may be physically limited in the ability to exercise, may leads a sedentary lifestyle, and/or may not have or is not suspected of having Parkinson's disease.

In another embodiment, there is provided a method of preventing or treating metabolic disorder or diabetes comprising administering to a subject in need thereof a bis (3'-indolyl)-containing molecule, or a method of preventing or treating obesity, or inducing weight loss comprising administering to a subject in need thereof a bis (3'-indolyl)-containing molecule, or a method of improving glucose tolerance, enhancing glucose uptake and/or treating or preventing fatty liver disease, hyperglycemia, hyperlipidemia, or hyperinsulinemia comprising administering to a subject in need thereof a bis (3'-indolyl)-containing molecule, or a method of increasing insulin sensitivity comprising administering to a subject in need thereof a bis (3'-indolyl)-containing molecule, or a method of increasing energy expenditure comprising administering to a subject in need thereof a bis (3'-indolyl)-containing molecule. The bis (3'-indolyl)-containing molecule may be a 1,1-bis(3'-indolyl)-1-(p-substituted phenyl)methane compound, amodiaquine or a derivative or analog thereof. The subject may be obese, overweight or in need of or desires weight loss, may be physically limited in the ability to exercise, may leads a sedentary lifestyle, and/or may not have or is not suspected of having Parkinson's disease.

For any of the foregoing methods, administering may be comprises oral, intravenous, subcutaneous, intramuscular, transdermal, topical or inhalation administration. The subject may be a human or a non-human mammal. Administering may be performed more than once, such as on a chronic basis, including daily, weekly, every other week or monthly. The methods may further comprise providing a second agent that normalizes metabolism, such as an anti-inflammatory agent, insulin or leptin.

In yet another embodiment, there is provided a method of mimicking exercise in a subject comprising administering to said subject a Nurr1 agonist. The Nun 1 agonist may be a bis (3'-indolyl)-containing molecule, such as a 1,1-bis(3'-indolyl)-1-(p-substituted phenyl)methane compound, amodiaquine or a derivative or analog thereof. Administering may be comprises oral, intravenous, subcutaneous, intramuscular, transdermal, topical or inhalation administration. The subject may be a human or a non-human mammal. Administering may be performed more than once, such as on a chronic basis, including daily, weekly, every other week or monthly.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIGS. 1A-H. Analysis of Nurr1-mTg mice. (FIG. 1A) Expression of Nurr1 mRNA in skeletal muscle of WT and Nurr1-mTg (Tg) mice as detected by qRT-PCR. (FIG. 1B) Weight gain of WT and Nurr1-mTg mice on normal chow over time. (FIG. 1C) Body composition of WT and Nurr1-mTg mice on normal chow. (FIG. 1D) Weight gain of WT and Nurr1-mTg mice on high fat diet (HFD) over time. (FIG. 1E) Glucose tolerance tests of WT and Nurr1-mTg mice on normal chow and HFD. (FIG. 1F) Serum insulin levels after 10 weeks on HFD in postpandrial state. (FIG. 1G) Serum free fatty acid levels after 10 weeks on HFD in postpandrial state. (FIG. 1H) Serum triglyceride (TRIG) levels after 10 weeks on HFD in postpandrial state. Data are represented as mean±SEM. n=10 for HFD FIGS. 2A-D. Resistance of Nurr1-mTg mice to hepatic steatosis. (FIG. 2A) Livers of WT and Nurr1-mTg mice after 10 weeks on HFD. Note extreme steatosis of WT liver and normal appearance of Nurr1-mTg liver. (FIG. 2B) Liver weights. (FIG. 2C) Histological sections of livers of WT and Nurr1-mTg mice stained with H&E (upper) and Oil Red O (lower). (FIG. 2D) Quantification of liver triglyceride levels.

FIGS. 3A-D. Changes in skeletal muscle gene expression of Nurr1-mTg mice. (FIG. 3A) Expression of GLUT4 mRNA in skeletal muscle of WT and Nurr1-mTg mice as detected by qRT-PCR. (FIG. 3B) Detection of glycogen in skeletal muscle of WT and Nurr1-mTg mice by PAS staining. (FIG. 3C) Quantification of glycogen content of skeletal muscle of WT and Nurr1-mTg mice. (FIG. 3D) WT and Nurr1-mTg mice at 6 weeks of age were subjected to a wheel running regimen. Nurr1-mTg mice showed enhanced endurance, measured by total distance run per hour.

(FIG. 4A) Regimen for treatment of mice with AQ. (FIG. 4B) Effect of AQ on weight gain of mice on normal chow and HFD. (FIG. 4C) AQ does not affect food intake of WT mice. (FIG. 4D) Effect of AQ on body composition of mice on normal chow and HFD. (FIG. 4E) Effect of AQ on glucose tolerance. (FIG. 4F) Effect of AQ on insulin tolerance. (FIG. 4G) Serum insulin levels after 10 weeks on HFD in postpandrial state. (FIG. 4H) Serum triglyceride (TRIG) levels after 10 weeks on HFD in postpandrial state. (FIG. 4I) Average oxygen consumption per hour during the light/dark cycle normalized to lean mass. (FIG. 4J) Average carbon dioxide production per hour during the light/dark cycle normalized to lean mass. (FIG. 4K) Respiratory exchange ratio. (FIG. 4L) AQ prevents hepatic steatosis in WT mice on HFD. (FIG. 4M) Quantification of liver triglyceride levels.

FIGS. 5A-F. Nurr1 agonist reverts hepatic steatosis in obese mouse models. (FIG. 5A) Picture of mice (WT-NC-CTL, Ob/Ob-CTL, Ob/Ob-AQ). (FIG. 5B) Effect of AQ on ob/ob mice body weight at the start and the end. (FIG. 5C) Effect of AQ on weight gain of ob/ob mice. (FIG. 5D) AQ does not affect food intake of ob/ob mice. (FIG. 5E) AQ recovers hepatic steatosis ob/ob mice to normal levels. (FIG. 5F) Quantification of liver triglyceride levels.

FIGS. 9A-F. A putative Nurr1 agonist IP7e confers resistance to obesity and prevents HFD. (FIG. 9A) Regimen for treatment of mice with IP7e. (FIG. 9B) Effect of IP7 on weight gain of mice on normal chow and HFD. (FIG. 9C) IP7 does not affect food intake of WT mice. (FIG. 9D) Effect of IP7e on glucose tolerance. (FIG. 9E) IP7e prevents hepatic steatosis in WT mice on HFD. (FIG. 9F) Quantification of liver triglyceride levels.

DETAILED DESCRIPTION

Figure 4A:
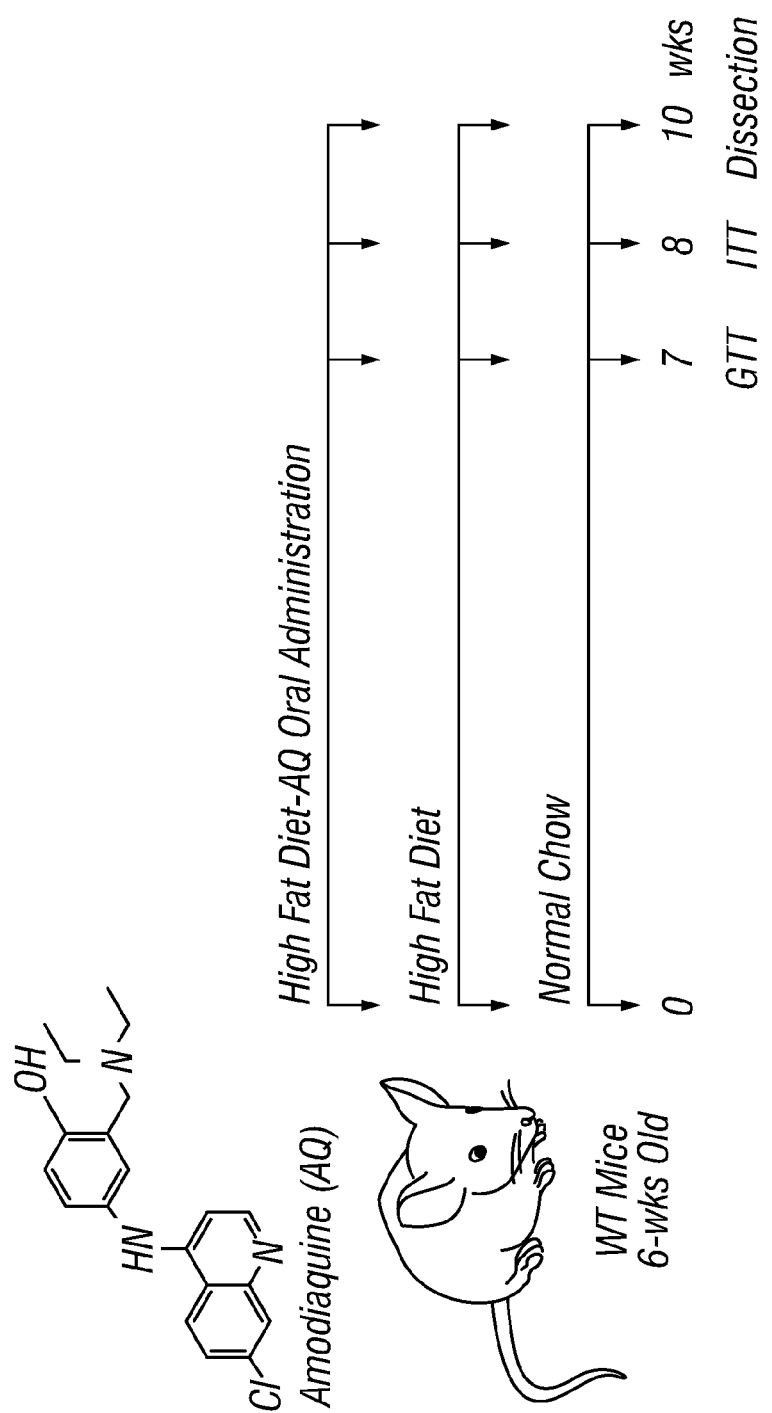
FIGS. 4A-M. A putative Nurr1 agonist AQ confers resistance to obesity and prevents HFD.

Through the generation of transgenic mice that over-express Nurr1 in skeletal muscle, the inventors now show that this orphan nuclear receptor can potently stimulate muscle glucose uptake and thereby normalize glucose and insulin levels and confer resistance to hepatic steatosis in obese mice. Transgenic over-expression of Nurr1 in skeletal muscle also confers an endurance phenotype, enabling mice to run further in a regimen of forced wheel running. Moreover, treatment of mice with a putative NURR1 agonist enhances systemic energy metabolism and prevents obesity and hepatic steatosis in ob/ob mice. These findings reveal a transcriptional basis for metabolic syndrome and the beneficial effects of exercise on systemic metabolism and suggest point to a potential pharmacologic approach for normalizing metabolism under conditions of caloric excess. These and other aspects of the disclosure are set out in detail below.

I. NURR1

The Nuclear receptor related 1 protein (NURR1) also known as NR4A2 (nuclear receptor subfamily 4, group A, member 2) is a protein that in humans is encoded by the NR4A2 gene. NURR1 is a member of the nuclear receptor family of intracellular transcription factors. The human mRNA sequence is at accession no. NM_006186, while the human protein sequence is at accession no. NP_006177.

NURR1 plays a key role in the maintenance of the dopaminergic system of the brain. Mutations in this gene have been associated with disorders related to dopaminergic dysfunction, including Parkinson's disease, schizophrenia, and manic depression. Misregulation of this gene may be associated with rheumatoid arthritis. Four transcript variants encoding four distinct isoforms have been identified for this gene. Additional alternate splice variants may exist, but their full-length nature has not been determined.

Research has been conducted on Nurr1's role in inflammation, and may provide important information in treating disorders caused by dopaminergic neuron disease. Inflammation in the CNS can result from activated microglia (macrophage analogs for the central nervous system) and other pro-inflammatory factors, such as bacterial lipopolysaccharide (LPS). LPS binds to toll-like receptors (TLR), which induces inflammatory gene expression by promoting signal-dependent transcription factors. To determine which cells are dopaminergic, experiments measured the enzyme tyrosine hydroxylase (TH), which is needed for dopamine synthesis. It has been shown that Nurr1 protects dopaminergic neurons from LPS-induced inflammation, by reducing inflammatory gene expression in microglia and astrocytes. When a short hairpin for Nurr1 was expressed in microglia and astrocytes, these cells produced inflammatory mediators, such as TNFa, NO synthase and IL-1β, supporting the conclusion that reduced Nurr1 promotes inflammation and leads to cell death of dopaminergic neurons. Nurr1 interacts with the transcription factor complex NF-κB-p65 on the inflammatory gene promoters. However, Nurr1 is dependent on other factors to be able to participate in these interactions. Nurr1 needs to be sumoylated and its co-regulating factor, glycogen synthase kinase 3, needs to be phosphorylated for these interactions to occur. Sumolyated Nurr1 recruits CoREST, a complex made of several proteins that assembles chromatin-modifying enzymes. The Nurr1/CoREST complex inhibits transcription of inflammatory genes.

One investigation conducted research on the structure and found that Nurr1 does not contain a ligand-binding cavity but a patch filled with hydrophobic side chains. Non-polar amino acid residues of Nurr1's co-regulators, SMRT and NCoR, bind to this hydrophobic patch. Analysis of tertiary structure has shown that the binding surface of the ligand-binding domain is located on the grooves of the 11th and 12th alpha helices. This study also found essential structural components of this hydrophobic patch, to be the three amino acids residues, F574, F592, L593; mutation of any these three inhibits LBD activity.

Nurr1 induces tyrosine hydroxylase (TH) expression, which eventually leads to differentiation into dopaminergic neurons. Nurr1 has been demonstrated to induce differentiation in CNS precursor cells in vitro but they require additional factors to reach full maturity and dopaminergic differentiation. Therefore, Nurr1 modulation may be promising for generation of dopaminergic neurons for Parkinson's disease research, yet implantation of these induced cells as therapy treatments, has had limited results. Nuclear receptor related 1 protein has been shown to interact with retinoic acid receptor alpha and retinoic acid receptor beta.

II. DISEASE STATES AND CONDIDITIONS SUITABLE FOR TREATMENT

As discussed above, the inventors have determined that activation of Nurr1 results in significant metabolic alterations that can benefit a number of diseases and disorders. Some of these are discussed below.

A. Hepatic Steatosis

Fatty liver, also known as fatty liver disease (FLD), is a reversible condition wherein large vacuoles of triglyceride fat accumulate in liver cells via the process of steatosis (i.e., abnormal retention of lipids within a cell). Despite having multiple causes, fatty liver can be considered a single disease that occurs worldwide in those with excessive alcohol intake and the obese (with or without effects of insulin resistance). The condition is also associated with other diseases that influence fat metabolism. When this process of fat metabolism is disrupted, the fat can accumulate in the liver in excessive amounts, thus resulting in a fatty liver. It is difficult to distinguish alcoholic FLD from nonalcoholic FLD, and both show microvesicular and macrovesicular fatty changes at different stages.

Accumulation of fat may also be accompanied by a progressive inflammation of the liver (hepatitis), called steatohepatitis. By considering the contribution by alcohol, fatty liver may be termed alcoholic steatosis or non-alcoholic fatty liver disease (NAFLD), and the more severe forms as alcoholic steatohepatitis (part of alcoholic liver disease) and non-alcoholic steatohepatitis (NASH).

Fatty liver (FL) is commonly associated with alcohol or metabolic syndrome (diabetes, hypertension, obesity, and dyslipidemia), but can also be due to any one of many causes: Metabolic, Nutritional, Drugs and Toxins, Alcoholic and Other. Metabolic forms include abetalipoproteinemia, glycogen storage diseases, Weber-Christian disease, acute fatty liver of pregnancy, and lipodystrophy. Nutritional forms include malnutrition, total parenteral nutrition, severe weight loss, refeeding syndrome, jejunoileal bypass, gastric bypass, jejunal diverticulosis with bacterial overgrowth. Drugs and toxins amiodarone, methotrexate, diltiazem, expired tetracycline, highly active antiretroviral therapy, glucocorticoids, tamoxifen, environmental hepatotoxins (e.g., phosphorus, mushroom poisoning). Alcoholism is one of the major cause of fatty liver due to production of toxic metabolites like aldehydes during metabolism of alcohol in the liver. This phenomenon most commonly occurs with chronic alcoholism. Other causes include inflammatory bowel disease, HIV, hepatitis C (especially genotype 3), and alpha 1-antitrypsin deficiency.

Fatty change represents the intracytoplasmatic accumulation of triglycerides (neutral fats). At the beginning, the hepatocytes present small fat vacuoles (liposomes) around the nucleus (microvesicular fatty change). In this stage, liver cells are filled with multiple fat droplets that do not displace the centrally located nucleus. In the late stages, the size of the vacuoles increases, pushing the nucleus to the periphery of the cell, giving characteristic signet ring appearance (macrovesicular fatty change). These vesicles are welldelineated and optically "empty" because fats dissolve during tissue processing. Large vacuoles may coalesce and produce fatty cysts, which are irreversible lesions. Macrovesicular steatosis is the most common form and is typically associated with alcohol, diabetes, obesity, and corticosteroids. Acute fatty liver of pregnancy and Reye's syndrome are examples of severe liver disease caused by microvesicular fatty change. The diagnosis of steatosis is made when fat in the liver exceeds 5-10% by weight.

Defects in fatty acid metabolism are responsible for pathogenesis of FLD, which may be due to imbalance in energy consumption and its combustion, resulting in lipid storage, or can be a consequence of peripheral resistance to insulin, whereby the transport of fatty acids from adipose tissue to the liver is increased. Impairment or inhibition of receptor molecules (PPAR-α, PPAR-γ and SREBP1) that control the enzymes responsible for the oxidation and synthesis of fatty acids appears to contribute to fat accumulation. In addition, alcoholism is known to damage mitochondria and other cellular structures, further impairing cellular energy mechanism. On the other hand, nonalcoholic FLD may begin as excess of unmetabolised energy in liver cells. Hepatic steatosis is considered reversible and to some extent nonprogressive if the underlying cause is reduced or removed.

Severe fatty liver is sometimes accompanied by inflammation, a situation referred to as steatohepatitis. Progression to alcoholic steatohepatitis (ASH) or Non-alcoholic steatohepatitis (NASH) depends on the persistence or severity of the inciting cause. Pathological lesions in both conditions are similar. However, the extent of inflammatory response varies widely and does not always correlate with degree of fat accumulation. Steatosis (retention of lipid) and onset of steatohepatitis may represent successive stages in FLD progression.

Liver disease with extensive inflammation and a high degree of steatosis often progresses to more severe forms of the disease. Hepatocyte ballooning and necrosis of varying degrees are often present at this stage. Liver cell death and inflammatory responses lead to the activation of stellate cells, which play a pivotal role in hepatic fibrosis. The extent of fibrosis varies widely. Perisinusoidal fibrosis is most common, especially in adults, and predominates in zone 3 around the terminal hepatic veins.

The progression to cirrhosis may be influenced by the amount of fat and degree of steatohepatitis and by a variety of other sensitizing factors. In alcoholic FLD, the transition to cirrhosis related to continued alcohol consumption is well-documented, but the process involved in nonalcoholic FLD is less clear.

Most individuals are asymptomatic and are usually discovered incidentally because of abnormal liver function tests or hepatomegaly noted in unrelated medical conditions. Elevated liver biochemistry is found in 50% of patients with simple steatosis. The serum alanine transaminase level usually is greater than the aspartate transaminase level in the nonalcoholic variant and the opposite in alcoholic FLD (AST:ALT more than 2:1).

Imaging studies are often obtained during the evaluation process. Ultrasonography reveals a "bright" liver with increased echogenicity. Medical imaging can aid in diagnosis of fatty liver; fatty livers have lower density than spleens on computed tomography (CT), and fat appears bright in T1-weighted magnetic resonance images (MRIs). No medical imagery, however, is able to distinguish simple steatosis from advanced NASH. Histological diagnosis by liver biopsy is sought when assessment of severity is indicated.

The treatment of fatty liver depends on its cause, and, in general, treating the underlying cause will reverse the process of steatosis if implemented at an early stage. Two known causes of fatty liver disease are an excess consumption of alcohol and a prolonged diet containing foods with a high proportion of calories coming from lipids. For the patients with non-alcoholic fatty liver disease with pure steatosis and no evidence of inflammation, a gradual weight loss is often the only recommendation. In more serious cases, medications that decrease insulin resistance, hyperlipidemia, and those that induce weight loss have been shown to improve liver function. For advanced patients with non-alcoholic steatohepatitis (NASH), there are no currently available therapies.

Up to 10% of people with cirrhotic alcoholic FLD will develop hepatocellular carcinoma. The overall incidence of liver cancer in nonalcoholic FLD has not yet been quantified, but the association is well-established. The prevalence of FLD in the general population ranges from 10% to 24% in various countries. However, the condition is observed in up to 75% of obese people, 35% of whom progressing to NAFLD, despite no evidence of excessive alcohol consumption. FLD is the most common cause of abnormal liver function tests in the United States.

B. Diabetes

Type I diabetes is a form of diabetes mellitus. Type I diabetes is an autoimmune disease that results in the permanent destruction of insulin-producing β cells of the pancreas. Type I is lethal unless treatment with exogenous insulin via injections replaces the missing hormone, or a functional replacement for the destroyed pancreatic beta cells is provided (such as via a pancreas transplant).

In contrast, diabetes mellitus type 2 (formerly non-insulin-dependent diabetes mellitus or adult-onset diabetes) is a metabolic disorder that is characterized by high blood glucose in the context of insulin resistance and relative insulin deficiency. The classic symptoms are excess thirst, frequent urination, and constant hunger. Type 2 diabetes makes up about 90% of cases of diabetes with the other 10% due primarily to diabetes mellitus type 1 and gestational diabetes. Obesity is thought to be the primary cause of type 2 diabetes in people who are genetically predisposed to the disease.

Type 2 diabetes is initially managed by increasing exercise and dietary modification. However, there are several classes of anti-diabetic medications available when exercise and diet alone fail. Metformin is generally recommended as a first line treatment as there is good evidence that it decreases mortality. Injections of insulin may either be added to oral medication or used alone. Other classes of medications used to treat type 2 diabetes are sulfonylureas, nonsulfonylurea secretagogues, alpha glucosidase inhibitors, and thiazolidinediones. Metformin however should not be used in those with severe kidney or liver problems.

When insulin is used, a long-acting formulation is typically added initially at night, while oral medications are continued. Doses are then increased to effect. When nightly insulin is insufficient twice daily insulin may achieve better control. The long acting insulins, glargine and detemir, do not appear much better than NPH but have a significantly greater cost making them as of 2010 not cost effective. In those who are pregnant insulin is generally the treatment of choice.

Rates of diabetes have increased markedly over the last 50 years in parallel with obesity. As of 2010 there are approximately 285 million people with the disease compared to around 30 million in 1985. Long-term complications from high blood sugar can include heart attacks, strokes, diabetic retinopathy where eyesight is affected, kidney failure which may require dialysis, and poor circulation of limbs leading to amputations. The acute complication ketoacidosis is uncommon unlike in type 1 diabetes, nonketonic hyperglycemia however may occur. The classic symptoms of diabetes are polyuria (frequent urination), polydipsia (increased thirst), polyphagia (increased hunger), and weight loss.

Type 2 diabetes is typically a chronic disease, associated with a ten year shorter life expectancy. This is partly due to a number of complications with which it is associated including: two to four times the risk of cardiovascular disease and stroke, a 20-fold increase in lower limb amputations, and increased rates of hospitalizations. In the developed world, and increasingly elsewhere, type 2 diabetes is the largest cause of non-traumatic blindness and kidney failure, as compared to non-diabetics. It has also been associated with an increased risk of cognitive dysfunction and dementia through disease processes such as Alzheimer's disease and vascular dementia. Other complications include: acanthosis nigricans, sexual dysfunction, and frequent infections.

The development of type 2 diabetes is caused by a combination of lifestyle and genetic factors. While some are under personal control, such as diet and obesity, others such as age, gender, and genetics are not. A lack of sleep has been linked to type 2 diabetes as has nutritional status during fetal development.

The most useful laboratory test to distinguish type I from type II diabetes is the C-peptide assay, which is a measure of endogenous insulin production since external insulin (to date) has included no C-peptide. However, C-peptide is not absent in type I diabetes until insulin production has fully ceased, which may take months. The presence of anti-islet antibodies (to Glutamic Acid Decarboxylase, Insulinoma Associated Peptide-2 or insulin), or lack of insulin resistance, determined by a glucose tolerance test, would also be suggestive of type 1. As opposed to that, many type 2 diabetics still produce insulin internally, and all have some degree of insulin resistance. Testing for GAD 65 antibodies has been proposed as an improved test for differentiating between type 1 and type 2 diabetes.

C. Metabolic Syndrome

Metabolic syndrome is a clustering of at least three of five of the following medical conditions: abdominal (central) obesity, elevated blood pressure, elevated fasting plasma glucose, high serum triglycerides, and low high-density lipoprotein (HDL) levels. Metabolic syndrome is associated with the risk of developing cardiovascular disease and diabetes. Some studies have shown the prevalence in the USA to be an estimated 34% of the adult population, and the prevalence increases with age.

Metabolic syndrome and prediabetes may be the same disorder, just diagnosed by a different set of biomarkers. The syndrome is thought to be caused by an underlying disorder of energy utilization and storage. The cause of the syndrome is an area of on-going medical research. The main sign of metabolic syndrome is central obesity (also known as visceral, male-pattern or apple-shaped adiposity), overweight with adipose tissue accumulation particularly around the waist and trunk. Other signs of metabolic syndrome include high blood pressure, decreased fasting serum HDL cholesterol, elevated fasting serum triglyceride level (VLDL triglyceride), impaired fasting glucose, insulin resistance, or prediabetes.

Associated conditions include hyperuricemia, fatty liver (especially in concurrent obesity) progressing to non-alcoholic fatty liver disease, polycystic ovarian syndrome (in women), erectile dysfunction (in men), and acanthosis nigricans.

The exact mechanisms of the complex pathways of metabolic syndrome are under investigation. The pathophysiology is very complex and has been only partially elucidated. Most patients are older, obese, sedentary, and have a degree of insulin resistance. Stress can also be a contributing factor. The most important risk factors are diet (particularly sugar-sweetened beverage consumption), genetics, aging, sedentary behavior or low physical activity, disrupted chronobiology/sleep, mood disorders/psychotropic medication use, and excessive alcohol use. There is debate regarding whether obesity or insulin resistance is the cause of the metabolic syndrome or if they are consequences of a more far-reaching metabolic derangement. A number of markers of systemic inflammation, including C-reactive protein, are often increased, as are fibrinogen, interleukin 6, tumor necrosis factor-alpha (TNF-α), and others. Some have pointed to a variety of causes, including increased uric acid levels caused by dietary fructose.

It is generally accepted that the current food environment contributes to the development of metabolic syndrome: our diet is mismatched with our biochemistry. Weight gain is associated with metabolic syndrome. Rather than total adiposity, the core clinical component of the syndrome is visceral and/or ectopic fat (i.e., fat in organs not designed for fat storage) whereas the principal metabolic abnormality is insulin resistance. The continuous provision of energy via dietary carbohydrate, lipid, and protein fuels, unmatched by physical activity/energy demand creates a backlog of the products of mitochondrial oxidation, a process associated with progressive mitochondrial dysfunction and insulin resistance.

Recent research indicates prolonged chronic stress can contribute to metabolic syndrome by disrupting the hormonal balance of the hypothalamic-pituitary-adrenal axis (HPA-axis). A dysfunctional HPA-axis causes high cortisol levels to circulate, which results in raising glucose and insulin levels, which in turn cause insulin-mediated effects on adipose tissue, ultimately promoting visceral adiposity, insulin resistance, dyslipidemia and hypertension, with direct effects on the bone, causing "low turnover" osteoporosis. HPA-axis dysfunction may explain the reported risk indication of abdominal obesity to cardiovascular disease (CVD), type 2 diabetes and stroke. Psychosocial stress is also linked to heart disease.

Central obesity is a key feature of the syndrome, being both a symptom and a cause of it in that the increasing adiposity often reflected in high waist circumference both often results from and often contributes to insulin resistance. However, despite the importance of obesity, patients who are of normal weight may also be insulin-resistant and have the syndrome.

Physical inactivity is a predictor of CVD events and related mortality. Many components of metabolic syndrome are associated with a sedentary lifestyle, including increased adipose tissue (predominantly central); reduced HDL cholesterol; and a trend toward increased triglycerides, blood pressure, and glucose in the genetically susceptible. Compared with individuals who watched television or videos or used their computers for less than one hour daily, those who carried out these behaviors for greater than four hours daily have a twofold increased risk of metabolic syndrome.

Metabolic syndrome affects 60% of the U.S. population older than age 50. With respect to that demographic, the percentage of women having the syndrome is higher than that of men. The age dependency of the syndrome's prevalence is seen in most populations around the world.

It is common for there to be a development of visceral fat, after which the adipocytes (fat cells) of the visceral fat increase plasma levels of TNF-α and alter levels of a number of other substances (e.g., adiponectin, resistin, and PAI-1). TNF-α has been shown not only to cause the production of inflammatory cytokines, but also possibly to trigger cell signaling by interaction with a TNF-α receptor that may lead to insulin resistance. An experiment with rats fed a diet with 33% sucrose has been proposed as a model for the development of metabolic syndrome. The sucrose first elevated blood levels of triglycerides, which induced visceral fat and ultimately resulted in insulin resistance. The progression from visceral fat to increased TNF-α to insulin resistance has some parallels to human development of metabolic syndrome. The increase in adipose tissue also increases the number of immune cells present within, which play a role in inflammation. Chronic inflammation contributes to an increased risk of hypertension, atherosclerosis and diabetes.

The involvement of the endocannabinoid system in the development of metabolic syndrome is indisputable. Endocannabinoid overproduction may induce reward system dysfunction and cause executive dysfunctions (e.g., impaired delay discounting), in turn perpetuating unhealthy behaviors. The brain is crucial in development of metabolic syndrome, modulating peripheral carbohydrate and lipid metabolism.

The metabolic syndrome can be induced by overfeeding with sugar or fructose, particularly concomitantly with high-fat diet. The resulting oversupply of omega-6 fatty acids, particularly arachidonic acid (AA), is an important factor in the pathogenesis of metabolic syndrome. Arachidonic acid (with its precursor-linoleic acid) serve as a substrate to the production of inflammatory mediators known as eicosanoids, whereas the arachidonic acid-containing compound diacylglycerol (DAG) is a precursor to the endocannabinoid 2-arachidonoylglycerol (2-AG) while fatty acid amide hydrolase (FAAH) mediates the metabolism of arachidonic acid into anandamide. Anandamide can also be produced from N-acylphosphatidylethanolamine via several pathways. Anandamide and 2-AG can also be hydrolized into arachidonic acid, potentially leading to increased eicosanoid synthesis.

Metabolic syndrome is a risk factor for neurological disorders. Metabolomic studies suggest an excess of organic acids, impaired lipid oxidation byproducts, essential fatty acids and essential amino acids in the blood serum of affected patients. However, it is not entirely clear whether the accumulation of essential fatty acids and amino acids is the result of excessive ingestion or excess production by gut microbiota.

Various strategies have been proposed to prevent the development of metabolic syndrome. These include increased physical activity (such as walking 30 minutes every day), and a healthy, reduced calorie diet. Many studies support the value of a healthy lifestyle as above. However, one study stated these potentially beneficial measures are effective in only a minority of people, primarily due to a lack of compliance with lifestyle and diet changes. The International Obesity Taskforce states that interventions on a sociopolitical level are required to reduce development of the metabolic syndrome in populations.

The Caerphilly Heart Disease Study followed 2,375 male subjects over 20 years and suggested the daily intake of a pint (~568 ml) of milk or equivalent dairy products more than halved the risk of metabolic syndrome. Some subsequent studies support the authors' findings, while others dispute them. A systematic review of four randomized controlled trials found that a paleolithic nutritional pattern improved three of five measurable components of the metabolic syndrome in participants with at least one of the components.

The first line treatment is change of lifestyle (e.g., Dietary Guidelines for Americans and physical activity). However, if in three to six months of efforts at remedying risk factors prove insufficient, then drug treatment is frequently required. Generally, the individual disorders that compose the metabolic syndrome are treated separately. Diuretics and ACE inhibitors may be used to treat hypertension. Cholesterol drugs may be used to lower LDL cholesterol and triglyceride levels, if they are elevated, and to raise HDL levels if they are low. Use of drugs that decrease insulin resistance, e.g., metformin and thiazolidinediones, is controversial; this treatment is not approved by the U.S. Food and Drug Administration. Weight loss medications may result in weight loss. As obesity is often recognized as the culprit behind many of the additional symptoms, with weight loss and lifestyle changes in diet, physical activity, the need for other medications may diminish.

A 2003 study indicated cardiovascular exercise was therapeutic in approximately 31% of cases. The most probable benefit was to triglyceride levels, with 43% showing improvement; but fasting plasma glucose and insulin resistance of 91% of test subjects did not improve. Many other studies have supported the value of physical activity and dietary modifications to treat metabolic syndrome. Some natural compounds, like ursolic acid, have been suggested as a treatment for obesity/metabolic syndrome based on the results of extensive research involving animal models; it is argued, however, that there is still a lack of data regarding the use of ursolic acid in humans, as phase-II/III trials of that drug have not been carried so far.

Restricting the overall dietary carbohydrate intake is more effective in reducing the most common symptoms of metabolic syndrome than the more commonly prescribed reduction in dietary fat intake.

The combination preparation simvastatin/sitagliptin (marketed as Juvisync) was introduced in 2011 and the use of this drug was to lower LDL levels and as well as increase insulin levels. This drug could have been used to treat metabolic syndrome but was removed from the market by Merck in 2013 due to business reasons.

High-dose statins, recommended to reduce cardiovascular risk, have been associated with higher progression to diabetes, particularly in patients with metabolic syndrome. The biological mechanisms are not entirely understood, however, the plausible explanation may lie in competitive inhibition of glucose transport via the solute carrier (SLC) family of transporters (specifically SLCO1B1), important in statin pharmacokinetics.

D. Obesity

Obesity has become a major health problem in the United States and other developed nations. In the United States, 65% of the adult population is considered overweight or obese, and more than 30% of adults meet the criteria for obesity. The World Health Organization has estimated that more than 1 billion adults worldwide are overweight, with 300 million of these considered clinically obese. The incidence of obesity in children is also growing rapidly in many countries. Obesity is a major risk factor for cardiovascular disease, stroke, insulin resistance, type 2 diabetes, liver disease, neurodegenerative disease, respiratory diseases and other severe illnesses, and has been implicated as a risk factor for certain types of cancer including breast and colon cancer. Aside from its impacts on physical health, obesity has significant adverse effects on quality of life and psychological well-being. The incidence of obesity, already high, is likely to grow as a result of increasingly sedentary lifestyles in many countries. In addition, certain widely used psychiatric drugs, notably atypical antipsychotics, are associated with weight gain and increased risk of diabetes. Since these drugs must be used chronically to achieve adequate control of psychiatric symptoms, and treatment compliance in patients with mental disorders is frequently poor, these side effects present both a barrier to compliance and a significant additional health risk to patients.

Although it is well established that weight loss can be achieved through reduced caloric intake and increased physical activity, obesity has continued to be an intractable problem in Western countries, especially in the United States. The discovery of safe and effective drugs to induce weight loss has been a major research goal for decades. However, to date the drugs that have shown efficacy have been burdened with significant side effects or have shown only modest efficacy. For example, amphetamines have been used effectively as appetite suppressants but have a strong risk of dependence along with other side effects. The discovery of leptin, a peptide hormone that plays a major role in appetite regulation, was considered to be a potential breakthrough in the treatment of obesity, but in clinical trials, leptin was not effective. More recently, cannabinoid receptor antagonists were under development as anti-obesity drugs but showed unacceptable psychiatric side effects. Similarly, drugs designed to reduce fat absorption in the digestive tract have been associated with significant gastrointestinal side effects.

Thus, another aspect of the present disclosure concerns new methods and compounds for the treatment and prevention of obesity. Obesity is a medical condition in which excess body fat has accumulated to the extent that it may have an adverse effect on health. It is typically defined by body mass index (BMI) and may be further evaluated in terms of fat distribution via the waist-hip ratio and total cardiovascular risk factors. BMI is related to both percentage body fat and total body fat.

BMI is calculated by dividing the subject's mass by the square of his or her height (in metric units: kilograms/meters$^2$). The definitions established by the World Health Organization (WHO) in 1997 and published in 2000 are listed below:

| BMI | Classification |
|---|---|
| <18.5 | underweight |
| 18.5-24.9 | normal weight |
| 25.0-29.9 | overweight |
| 30.0-34.9 | class I obesity |
| 35.0-39.9 | class II obesity |
| ≥40.0 | class III obesity |

Obesity increases the risk of many physical and mental conditions. These comorbidities are most commonly shown in metabolic syndrome, a combination of medical disorders which includes: diabetes mellitus type 2, high blood pressure, high blood cholesterol, and high triglyceride levels.

A substantial body of research supports an association between obesity and a chronic, "smoldering" inflammatory state. Obesity is associated with overproduction of inflammatory cytokines and chronic activation of inflammatory signaling pathways, including the NF-kB pathway. Chronic inflammation in adipose tissue is linked with the development of insulin resistance in skeletal muscle. Chronic activation of the NF-κB pathway has been shown to induce insulin resistance and NF-κB inhibition has been proposed as a therapeutic strategy for the treatment of Type 2 diabetes.

In a fashion analogous to the development of insulin resistance, obesity has been associated with the development of resistance to the action of leptin. Leptin, a peptide hormone, has complex biological effects but one important site of action is the mediobasal hypothalamus. This structure of the brain is known to exert control over feeding behavior and energy homeostasis. Recently, oxidative stress and activation of the NF-κB pathway in the hypothalamus were shown to be linked to hypothalamic insulin and leptin resistance.

III. METHODS OF TREATMENT

A. Treatments

In a particular aspect, the present disclosure provides methods for the treatment of various conditions benefiting from Nurr1 activation. Treatment methods will involve administering to an individual having such a disease or condition an effective amount of a composition containing a compound capable of activating Nurr1. An effective amount is described, generally, as that amount sufficient to detectably and repeatedly to ameliorate, reduce, minimize or limit the extent of the disease/disorder, or any its symptoms. More specifically, it is envisioned that the treatment according to the present disclosure will reduce one or more sympstoms associated with hepatic steatosis, metabolic disorder or diabetes, or obesity. This may include improving glucose tolerance, enhancing glucose uptake, increasing insulin sensitivity and/or treating or preventing fatty liver disease, hyperglycemia, hyperlipidemia, or hyperinsulinemia.

Also, in a healthy individual, provision of Nurr1 agonist can increase energy expenditure and even mimic exercise.

B. Bis (3'-indolyl) Molecules

Bis (3'-indolyl)-containing molecules have been demonstrated to be activators of Nurr1 through binding to its ligand-binding domain.

Amodiaquine (trade names Camoquin, Flavoquine), a 4-aminoquinoline compound related to chloroquine, falls within this group of compounds. Amodiaquine is a histamine N-methyltransferase inhibitor, and has been used as an antimalarial and anti-inflammatory agent. Amodiaquine has been shown to be more effective than chloroquine in treating chloroquine-resistant *Plasmodium falciparum* malaria infections and may give more protection than chloroquine when used as weekly prophylaxis. Amodiaquine, like chloroquine, is generally well tolerated. Although licensed, this drug is not marketed in the United States, but is widely available in Africa. Its use, therefore, is probably more practicable in long-term visitors and persons who will reside in Africa.

Amodiaquine is bioactivated hepatically to its primary metabolite, N-desethylamodiaquine, by the cytochrome p450 enzyme CYP2C8. Among amodiaquine users, several rare but serious side effects have been reported and linked to variants in the CYP2C8 alleles. CYP2C8*1 is characterized as the wild-type allele, which shows an acceptable safety profile, while CYP2C8*2, *3 and *4 all show a range of "poor metabolizer" phenotypes. People who are poor metabolizers of amodiaquine display lower treatment efficacy against malaria, as well as increased toxicity. Several studies have been conducted to determine the prevalence of CYP2C8 alleles amongst malaria patients in East Africa, and have tentatively shown the variant alleles have significant prevalence in that population. About 3.6% of the population studied showed high risk for a poor reaction to or reduced treatment outcomes when treated with amodiaquine.

De Miranda et al. (2015a) reported that novel 1,1-bis(3'-indolyl)-1-(p-substituted phenyl)methane (C-DIM) compounds that activate NR4A family nuclear receptors also suppress inflammatory gene expression in primary astrocytes and prevent loss of dopaminergic neurons in mice exposed to 1-methyl-4-phenyl-1,2,3,6-tetrahydropyridine and probenecid (MPTPp). To examine this mechanism, they treated transgenic NF-κB/EGFP reporter mice with MPTPp for 7 days (MPTPp7d) followed by daily oral gavage with either vehicle (corn oil; MPTPp14d) or C-DIMs containing p-methoxyphenyl (C-DIMS), p-hydroxyphenyl (C-DIMS), or p-chlorophenyl (C-DIM12) groups. Each compound conferred significant protection against progressive loss of dopaminergic neurons in the substantia nigra pars compacta (SNpc), even when given after 7 days of dosing with MPTPp. C-DIM12 had the greatest neuroprotective activity in MPTPp-treated mice, and was also the most potent compound in suppressing activation of microglia and astrocytes, expression of cytokines and chemokines in quantitative polymerase chain reaction (qPCR) array studies, and in reducing expression of NF-κB/EGFP in the SN. C-DIM12 prevented nuclear export of Nurr1 in dopaminergic neurons and enhanced expression of the Nurr1-regulated proteins tyrosine hydroxylase and the dopamine transporter. These data indicate that NR4A-active C-DIM compounds protect against loss of dopamine neurons in the MPTPp model of PD by preventing glial-mediated neuronal injury and by supporting a dopaminergic phenotype in TH-positive neurons in the SNpc.

De Miranda et al. (2015b) also reported that di-indolylmethane compounds (C-DIMs) activate or inactivate nuclear receptors, including Nurr1. They postulated that C-DIM12 [1,1-bis(3'-indolyl)-1-(p-chlorophenyl) methane] would suppress inflammatory signaling in microglia by a Nurr1-dependent mechanism. C-DIM12 inhibited lipopolysaccharide (LPS)-induced expression of NF-μB-regulated genes in BV-2 microglia including nitric oxide synthase (NOS2), interleukin-6 (IL-6), and chemokine (C-C motif) ligand 2 (CCL2), and the effects were attenuated by Nurr1-RNA interference. Additionally, C-DIM12 decreased NF-κB activation in NF-κB-GFP (green fluorescent protein) reporter cells and enhanced nuclear translocation of Nurr1 primary microglia. Chromatin immunoprecipitation assays indicated that C-DIM12 decreased lipopolysaccharide-induced p65 binding to the NOS2 promoter and concurrently enhanced binding of Nurr1 to the p65-binding site. Consistent with these findings, C-DIM12 also stabilized binding of the Corepressor for Repressor Element 1 Silencing Transcription Factor (CoREST) and the Nuclear Receptor Corepressor 2 (NCOR2). Collectively, these data identify C-DIM12 as a modulator of Nurr1 activity that results in inhibition of NF-κB-dependent gene expression in glial cells by stabilizing nuclear corepressor proteins, which reduces binding of p65 to inflammatory gene promoters.

C. Dosages

In certain embodiments, the compound or compounds of the present disclosure is/are administered to a subject. In another embodiment of the disclosure, the dose range of the compound(s) will be measured by body weight, for example, about 0.5 mg/kg body weight to about 500 mg/kg body weight. Those of skill will recognize the utility of a variety of dosage range, for example, 1 mg/kg body weight to 450 mg/kg body weight, 2 mg/kg body weight to 400 mg/kg body weight, 3 mg/kg body weight to 350 mg/kg body weighty, 4 mg/kg body weight to 300 mg/kg body weight, 5 mg/kg body weight to 250 mg/kg body weighty, 6 mg/kg body weight to 200 mg/kg body weight, 7 mg/kg body weight to 150 mg/kg body weighty, 8 mg/kg body weight to 100 mg/kg body weight, or 9 mg/kg body weight to 50 mg/kg body weight. Further, those of skill will recognize that a variety of different dosage levels will be of use, for example, 1 mg/kg, 2 mg/kg, 3 mg/kg, 4 mg/kg, 5 mg/kg, 7.5 mg/kg, 10 mg/kg, 12.5 mg/kg, 15 mg/kg, 17.5 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 120 mg/kg, 140 mg/kg, 150 mg/kg, 160 mg/kg, 180 mg/kg, 200 mg/kg, 225 mg/kg, 250 mg/kg, 275 mg/kg, 300 mg/kg, 325 mg/kg, 350 mg/kg, 375 mg/kg, 400 mg/kg, 450 mg/kg, 500 mg/kg, 550 mg/kg, 600 mg/kg, 700 mg/kg, 750 mg/kg, 800 mg/kg, 900 mg/kg, 1000 mg/kg, 1250 mg/kg, 1500 mg/kg, 1750 mg/kg, 2000 mg/kg, 2500 mg/kg, and/or 3000 mg/kg. Of course, all of these dosages are exemplary, and any dosage in-between these points is also expected to be of use in the disclosure. Any of the above dosage ranges or dosage levels may be employed for a compound or compounds of the present disclosure.

The treatments may include various "unit doses." Unit dose is defined as containing a predetermined-quantity of the therapeutic composition calculated to produce the desired responses in association with its administration, i.e., the appropriate route and treatment regimen. The quantity to be administered, and the particular route and formulation, are within the skill of those in the clinical arts. Also of import is the subject to be treated, in particular, the state of the subject and the protection desired. A unit dose need not be administered as a single injection but may comprise continuous infusion over a set period of time.

As is well known in the art, a specific dose level of active compounds for any particular patient depends upon a variety of factors including the activity of the specific compound employed, the age, body weight, general health, sex, diet, time of administration, route of administration, rate of excretion, drug combination, and the severity of the particular disease undergoing therapy. The person responsible for administration will determine the appropriate dose for the individual subject. Moreover, for human administration, preparations should meet sterility, pyrogenicity, general safety and purity standards as required by FDA Office of Biologics standards.

D. Formulations and Routes for Administration

Pharmaceutical compositions of the present disclosure comprise an effective amount of one or more candidate substance or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one candidate substance or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The compounds may be disposed in different types of carriers depending on whether the drug is to be administered in solid, liquid or aerosol form, and whether it need to be sterile for such routes of administration as injection. The present disclosure can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intramuscularly, subcutaneously, subconjunctival, intravesicularlly, mucosally, intrapericardially, intraumbilically, intraocularally, orally, locally, via inhalation (e.g., aerosol inhalation), via injection, via infusion, via continuous infusion, via localized perfusion bathing target cells directly, via a catheter, via a lavage, in creams, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present disclosure administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The drug may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use eye drops, nasal solutions or sprays, aerosols or inhalants in the present disclosure. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in particular embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the candidate substance is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the disclosure, the oral composition may be prepared as a syrup or elixir. A syrup or elixir, and may comprise, for example, at least one active agent, a sweetening agent, a preservative, a flavoring agent, a dye, a preservative, or combinations thereof.

In certain particular embodiments, an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations, which are suitable for other modes of administration, include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle, which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

E. Combination Treatment

In the context of the present disclosure, it is contemplated that the disclosed compounds may be used in combination with other therapies discussed herein to more effectively treat metabolic disorders and disease. When multiple therapeutic agents are administered, as long as the dose of the additional therapeutic agent does not exceed previously quoted toxicity levels, the effective amounts of the additional therapeutic agent may simply be defined as that amount effective to exert a therapeutic effect when administered to an animal in combination with the primary agent. This may be easily determined by monitoring the animal or patient and measuring those physical and biochemical parameters of health and disease that are indicative of the success of a given treatment. Such methods are routine in animal testing and clinical practice.

Compositions are provided in a combined amount effective to achieve a therapeutic benefit, as stated above. This process may involve administering a combination at the same time. This may be achieved by administering a single composition or pharmacological formulation that includes both agents, or by administering two distinct compositions or formulations, at the same time. Alternatively, treatment with one agent may precede or follow the other treatment by intervals ranging from minutes to weeks. In embodiments where the other treatment is administered separately to the patient, one would generally ensure that a significant period of time did not expire between the time of each delivery, such that the agents would still be able to exert an advantageously combined effect. In such instances, it is contemplated that one would contact the patient with both modalities within about 12-24 hr of each other and, more preferably, within about 6-12 hr of each other, with a delay time of only about 12 hr being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either or both agents will be desired. Various combinations may be employed, where a Nurr1 agonist is "A" and the other agent is "B," as exemplified below:

A/B/A B/A/B B/B/A A/A/B B/A/A A/B/B B/B/B/A B/B/A/B
A/A/B/B A/B/A/B A/B/B/A B/B/A/A B/A/B/A B/A/A/B B/B/B/A
A/A/A/B B/A/A/A A/B/A/A A/A/B/A A/B/B/B B/A/B/B B/B/A/B

Suitable "other" agents are discussed elsewhere in this document.

IV. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

Materials and Methods

Animals. Animals were housed in a pathogen free barrier facility with a 12 hour light/dark cycle and maintained on standard chow (2916 Teklad Global). The Nurr1 transcript was amplified from Invitrogen library with Nurr1-specific primers. Nurr1 was cloned into a plasmid containing the human skeletal muscle actin promoter and human GH (hGH) poly(A) signal. Nurr1 transgenic mice (referred as Nurr1-mTg) were backcrossed with C57/BL6J mice for more than four generations. C57BL/6J, ob/ob and db/db mice were obtained from Jackson Laboratories. Male mice were used in all experiments. For HFD (60% fat calories; D12492, Research Diet), mice were fed from the age of 5 weeks to the indicated times. Tissues were taken in the fed state except when otherwise mentioned.

Study approval. All experimental procedures involving animals in this study were reviewed and approved by the University of Texas Southwestern Medical Center's Institutional Animal Care and Use Committee.

Drug treatments. Amodiaquine was purchased from Acros Organics (Geel, Belgium), dissolved in water (7.5 mM), placed in water bottles and provided to mice ad libitum during the experimental period. Isoxazolo-pyridinone 7e (IP7e) was purchased from Millipore and dissolved in Tween 80 in a 10× stock solution. To obtain the final concentration (1×; 10 mg/kg) IP7e was dissolved in saline solution (0.9% NaCl). IP7e treatment by gavage was performed once a day. Control animals received the Tween 80 dissolved saline solution (0.9% NaCl, vehicle).

Plasmids. DNA fragments from the LBD region of Nurr, Nur77 and NOR-1 were isolated by PCR using mouse genomic DNA as a template and cloned into the luciferase reporter pGL3-SxUAS-GAL4 (Promega). The pcDNA3.1 Myc-based MEF2 expression vectors were previously reported. Primer sequences and plasmid construct designs are available upon request. Plasmids containing Nurr1, Nur77 were obtained from Invitrogen library.

RNA analysis. RNA was isolated from mouse tissues using TRIzol reagent (Invitrogen). Reverse Transcription-PCR (RT-PCR) was performed to generate cDNA. Primers for ribosomal 18S RNA served as internal controls for the quality of RNA. The sequence of primers is available upon request. Illumina RNA-seq analysis was performed by the University of Texas Southwestern Microarray Core Facility using RNA extracted from tissues of 12-week-old CTL or MED13-mKO on HFD or NC diet.

Histology. WAT, BAT and liver were isolated and fixed in 4% paraformaldehyde (PFA) and processed for H&E staining. For oil red O staining, liver tissues were fixed in 4% PFA overnight, incubated in 12% sucrose for 12 hours then in 18% sucrose overnight before being cryoembedded and sectioned by the UT Southwestern Histology Core Facility. For skeletal muscle fiber analysis, tissues were frozen in liquid-nitrogen precooled isopentane, and 8 µm sections were used for H&E and fiber type staining.

Metabolic chambers and whole-body composition analysis. Metabolic phenotyping of WT and Nurr1-mTg mice on HFD was performed using TSE metabolic chamber analysis by the Mouse Metabolic Phenotyping Core Facility at University of Texas Southwestern Medical Center. Thirteen week old mice on HFD were placed in TSE metabolic chambers for an initial 5 days acclimation period, followed by a 4.5 days experimental period with data collection. Whole-body composition parameters were measured by magnetic resonance imaging (MRI) using a Bruker Minispec mq10 system.

Plasma and tissue chemistry. Blood was collected using a 1 ml syringe coated in 0.5 M $K_2$EDTA and serum collected by centrifugation for 20 min at 1000×g. Insulin and leptin levels were measured by ELISA. Serum triglycerides levels were measured using the Ortho Vitros 250 chemistry system. To measure triglyceride in the liver and skeletal muscle, tissue specimens were frozen immediately after isolation and pulverized in liquid nitrogen with a cell crusher. Serum and tissue triglyceride levels were measured by Mouse Metabolic Phenotyping Core Facility at University of Texas Southwestern Medical Center.

Glucose uptake and insulin tolerance. Glucose tolerance test and insulin tolerance test were performed as previously described. For glucose tolerance test, mice were fasted for 6 hr and injected intraperitoneally with a glucose solution (0.15 g/ml, 158968 from Sigma-Aldrich, St. Louis, Mo.) at 1.5 g/kg body weight. Blood glucose concentrations were measured before and 15, 30, 60 and 90 min after glucose injection. For insulin tolerance test, mice prefasted for 6 hours were injected intraperitoneally with insulin (Human insulin 19278 from Sigma-Aldrich, St. Louis, Mo.) at 1.0 U/kg body weight. Blood glucose concentrations were measured before and 15, 30, 60 and 90 min after insulin injection.

Glycogen measurements. A glycogen colorimetric/fluorometric assay kit (Abcam 65620) was used as per the manufacturer's protocol to measure the quadriceps glycogen content in WT and Nurr1-mTg mice on HFD and NC diet.

Voluntary wheel running. Ten-week old Nurr1-mTg and corresponding WT littermates were randomly assigned to housing in individual cages with or without a running wheel for a total of 6 weeks. Completed wheel revolutions and time spent running were continuously monitored and recorded. Run distance over 24-hour periods was determined at the end.

Immunoblot analysis. Proteins were extracted from skeletal muscle of mice. Muscles were homogenized in RIPA Buffer, 10 mM NaF, 1 mM $Na_3VO4$, 1 mM PMSF and protease inhibitors tablet (Roche Diagnostics). Protein concentration was determined using a BCA protein assay kit (Thermo Scientific) and lysates analyzed by SDS-polyacrylamide gel electrophoresis and western blot analysis on PVDF membrane.

Statistical Analysis. All values are given as mean standard error. Differences between two groups were assessed using unpaired two-tailed Student's t-tests. $P<0.05$ was regarded as significant. Statistical analysis was performed in Excel (Microsoft).

Example 2

Results

Figure 7:
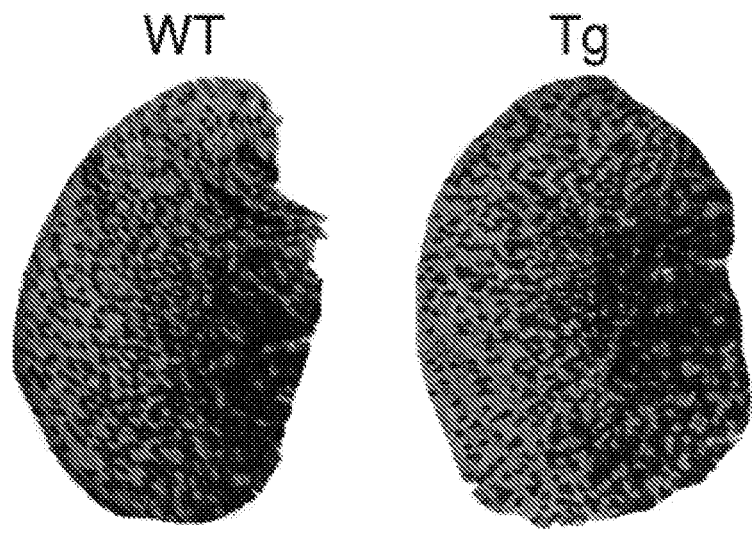
FIG. 7. Nurr1-mTg mice display similar muscle mitochondria abundance as WT mice on HFD. Succinate dehydrogenase staining of tibialis anterior muscle.

Muscle over-expression of Nurr1 enhances glucose handling in mice on HFD. To begin to investigate the potential involvement of Nurr1 in the control of skeletal muscle metabolism, the inventors generated transgenic mice that over-expressed Nurr1 specifically in skeletal muscle under control of the human skeletal muscle actin (HSA) promoter, which the inventors refer to as Nurr1-mTg mice. The inventors selected a transgenic line that expressed Nurr1 ~20-fold above normal levels in skeletal muscle (FIG. 1A). These mice showed the same weight gain as WT littermates with comparable lean and fat mass when maintained on normal chow and showed no overt abnormalities (FIGS. 1B-C). Skeletal muscle histological analysis showed similar mitochondrial abundance in Nurr1-mTg mice compared to WT mice (FIG. 7). When subjected to HFD, Nurr1-mTg mice gained weight comparably to WT littermates (FIG. 1D). When subjected to glucose tolerance tests, the Nurr1-mTg mice showed modest but significant improvement in glucose tolerance, whereas there was a pronounced improvement in glucose tolerance of mTg mice on HFD (FIG. 1E). HFD induced obesity leads commonly to hyperinsulinemia, which was observed in WT mice on HFD (FIG. 1F). However, serum insulin levels of Nurr1-mTG mice on HFD were significantly lower than in WT mice (FIG. 1F). Serum free fatty acid and triglyceride analyses were similar between Nurr1-mTg and WT mice on HFD (FIGS. 1G-H). Thus, Nurr1-mTg gained similar weight to WT mice on HFD, but displayed improved glucose tolerance and protection from hyperinsulinemia.

Resistance of Nurr1-mTg mice to hepatic steatosis. One of the consequences of HFD-induced obesity is the triglyceride (TRIG) accumulation in the liver also called hepatic steatosis. WT mice develop severe hepatic steatosis when maintained on HFD for 8 weeks (FIG. 2A). In contrast, livers from Nurr1-mTg mice on HFD appeared normal. Moreover, Nurr1-mTg mice displayed a dramatic reduction in liver weight compared to WT mice on HFD (FIG. 2B). To confirm the improved liver appearance of Nurr1-mTg on HFD, the inventors analyzed liver TRIG accumulation by hematoxylin/eosin (HE) and Oil red O staining. Nurr1-mTg mice displayed a dramatic reduction in hepatocyte TRIG accumulation compared to WT mice on HFD (FIG. 2C).

Biochemical measurements confirmed a pronounced 75% decrease in TRIG levels in livers from Nurr1-mTg mice compared to WT mice on HFD (FIG. 2D).

To determine if changes in food intake or body temperature might contribute to the resistance of Nurr1-mTg mice to hepatic TRIG accumulation, the inventors used metabolic cages to monitor the mice on HFD. Nurr1-mTg mice and WT mice showed similar activity, food intake, heat production. Taken together, these results suggest that Nurr1 overexpression in skeletal muscle leads to protection from hepatic steatosis independent of adipose tissues.

Changes in skeletal muscle gene expression in Nurr1-mTg mice. To begin to define the mechanistic basis of the resistance of Nurr1-mTg mice to hepatic steatosis, the inventors investigate gene expression profiles of glucose regulatory genes in skeletal muscle from WT and Nurr1-mTg mice on HFD. GLUT4, the main effector of insulin-stimulated glucose transport in skeletal muscle. Gene expression analysis showed that GLUT4 mRNA was specifically up-regulated in skeletal muscle of Nurr1-mTg mice, whereas expression of GLUT1 was unchanged (FIG. 3A). Skeletal muscle from Nurr1-mTg mice also showed increased expression of glucose 6-phosphatase d (G6pd), pointing to enhanced glucose metabolism. Histological staining of skeletal muscle for glycogen or detection of glycogen by biochemical assays confirmed that skeletal muscle of Nurr1-mTg mice had higher glycogen content (FIGS. 3B-C). Taken, together these results suggest that Nurr1 overexpression in skeletal muscle leads to enhanced glucose transport and storage as glycogen in skeletal muscle.

Enhanced endurance of Nurr1-mTg mice. Elevated skeletal muscle glycogen is considered on of the hallmark of endurance. Therefore, the increased glycogen content of skeletal muscle from Nurr1-mTg mice might be expected to enhance endurance in response to exercise. To test this possibility, the inventors subjected WT and Nurr1-mTg mice to a regimen of continuous wheel running for 8 weeks. As shown in FIG. 3D, Nurr1-mTg mice displayed enhanced wheel-running capacity, running ~20% further than WT mice before exhaustion. Taken, together these results suggest that Nurr1-mTg mice show an enhanced endurance in response to voluntary wheel exercise.

Figure 4B:
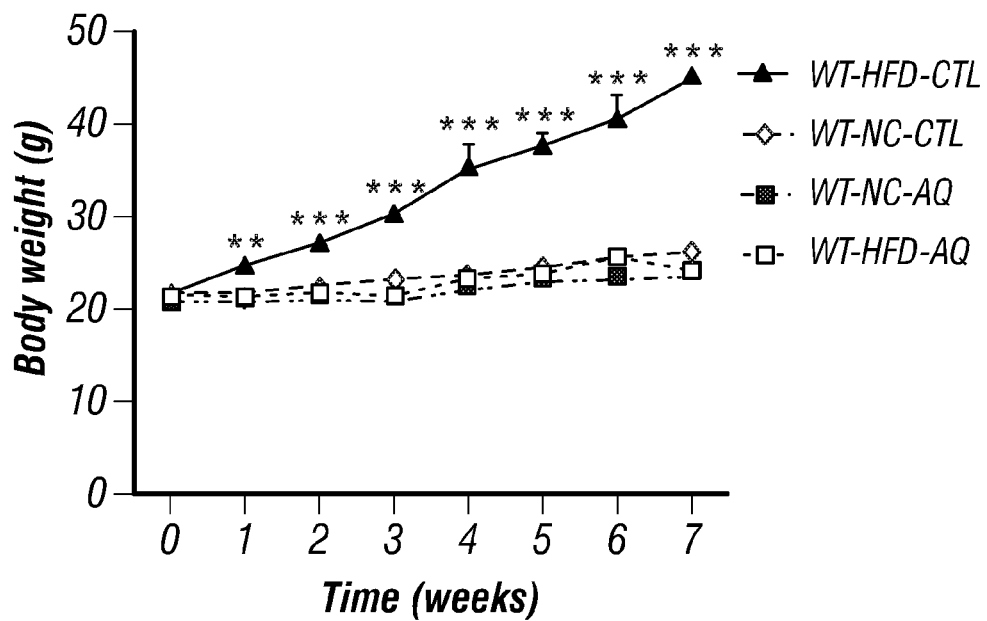
Figure 4C:
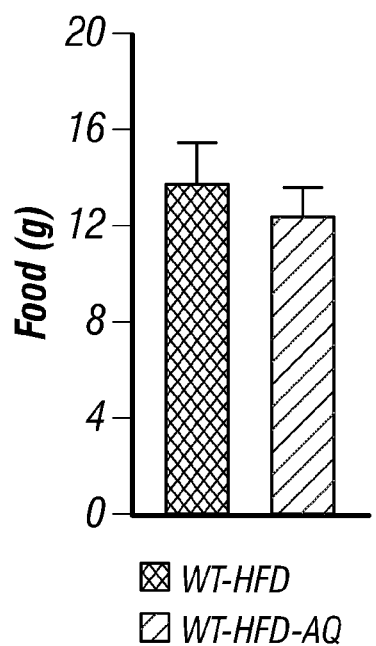
Figure 4D:
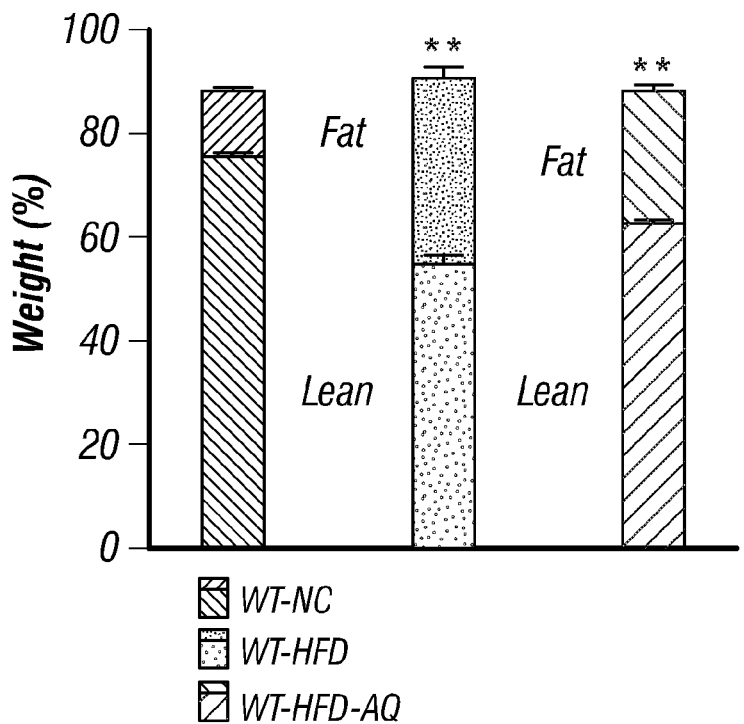
Figure 4E:
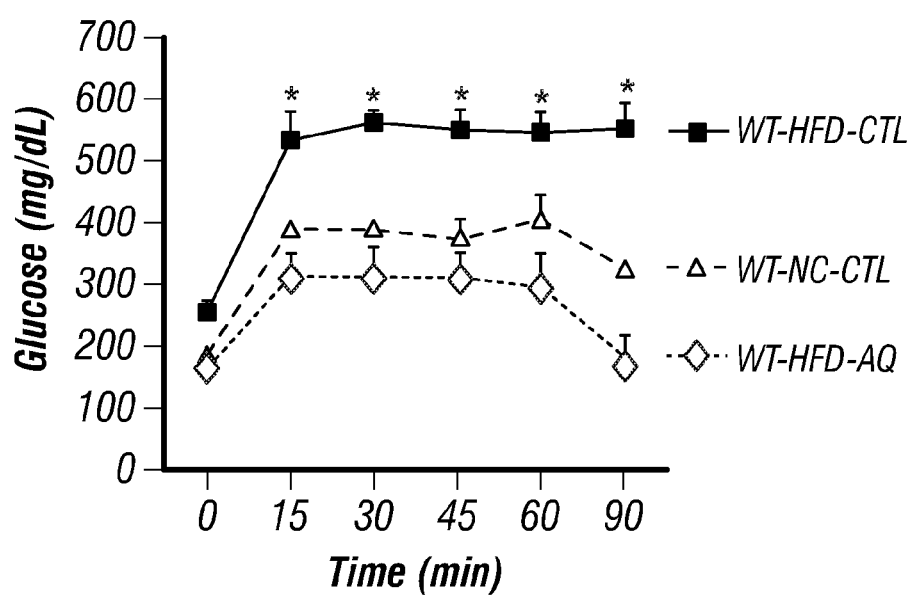
Figure 4F:
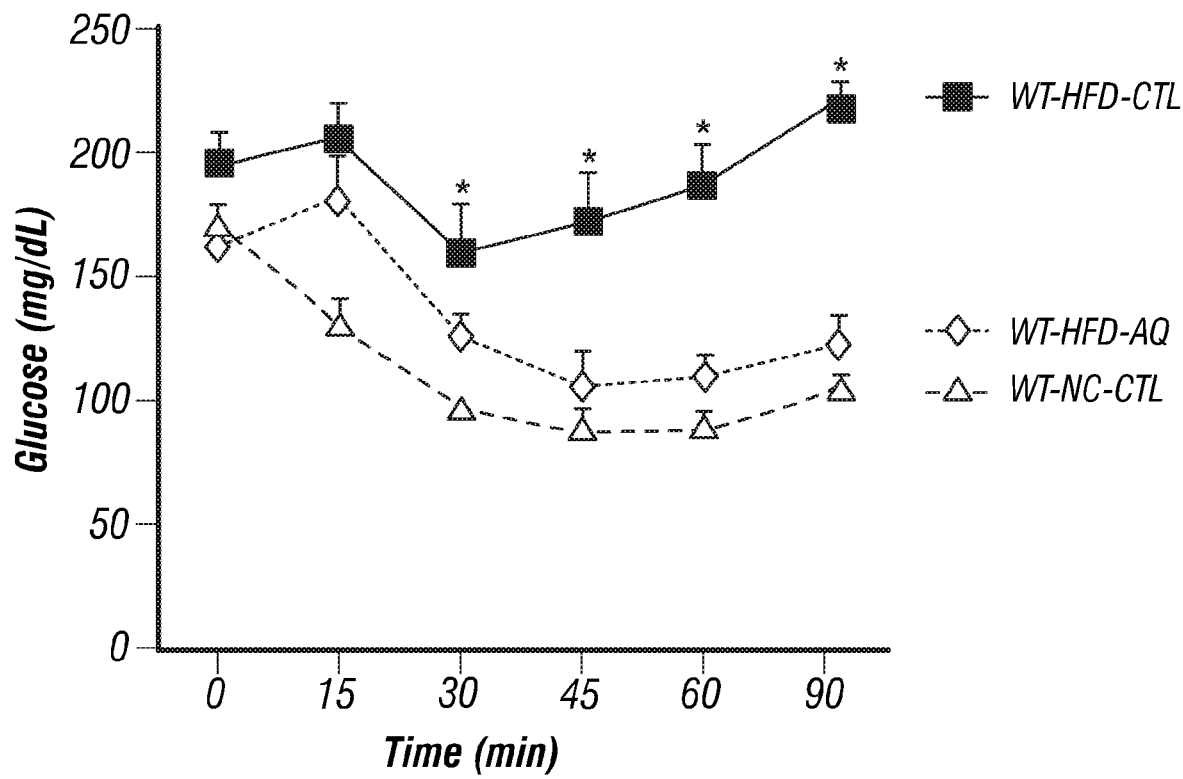
Figure 4G:
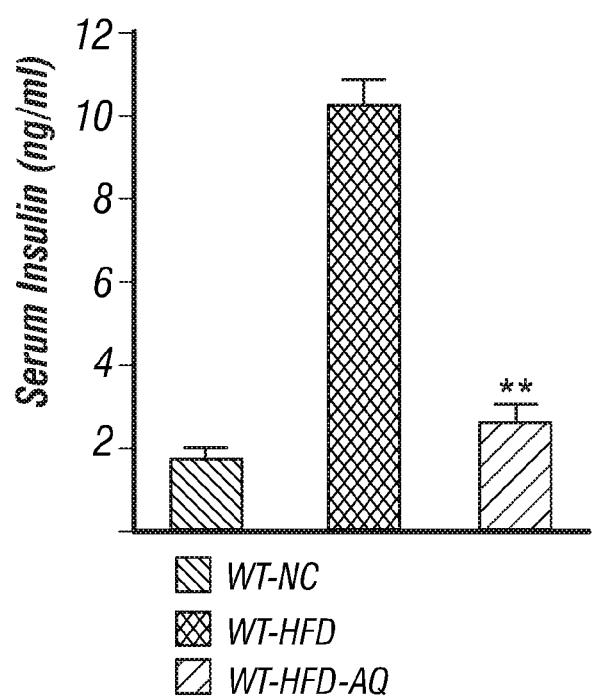
Figure 4H:
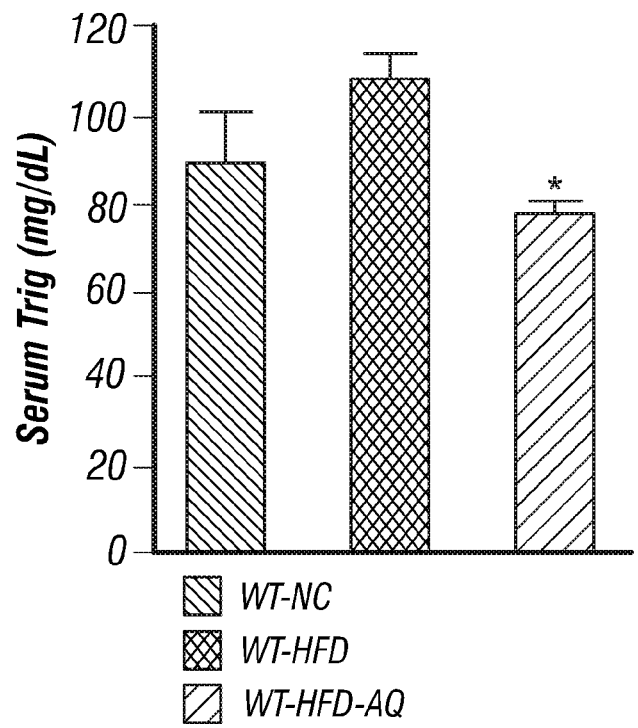
Figure 4I:
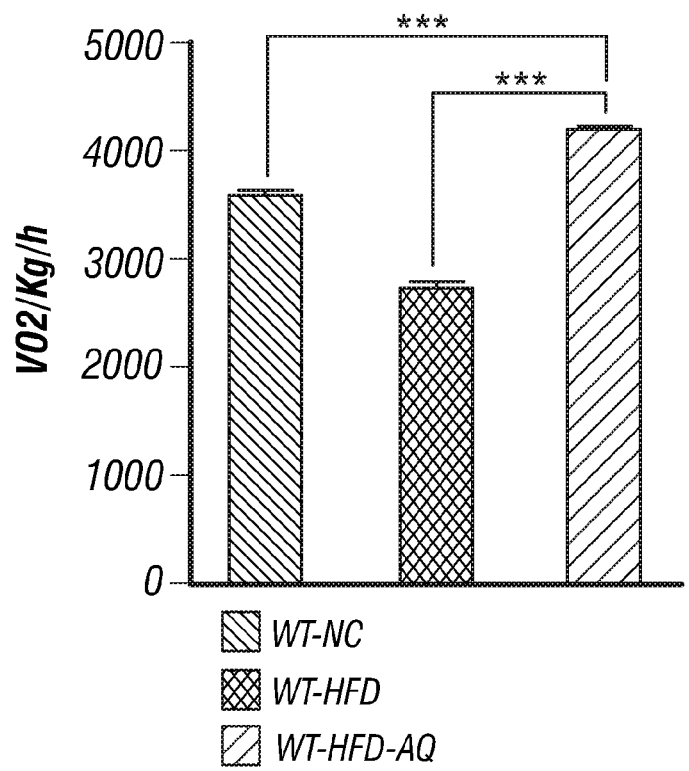
Figure 4J:
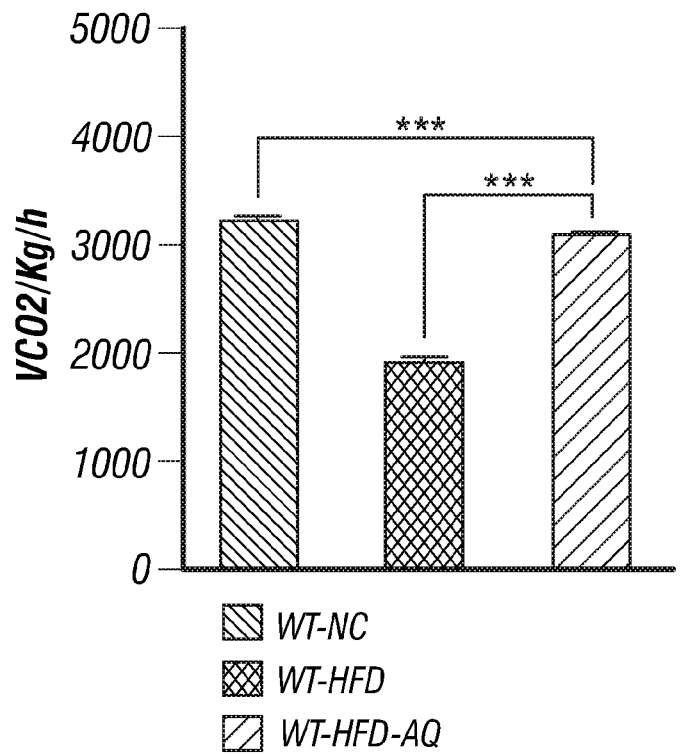
Figure 4K:
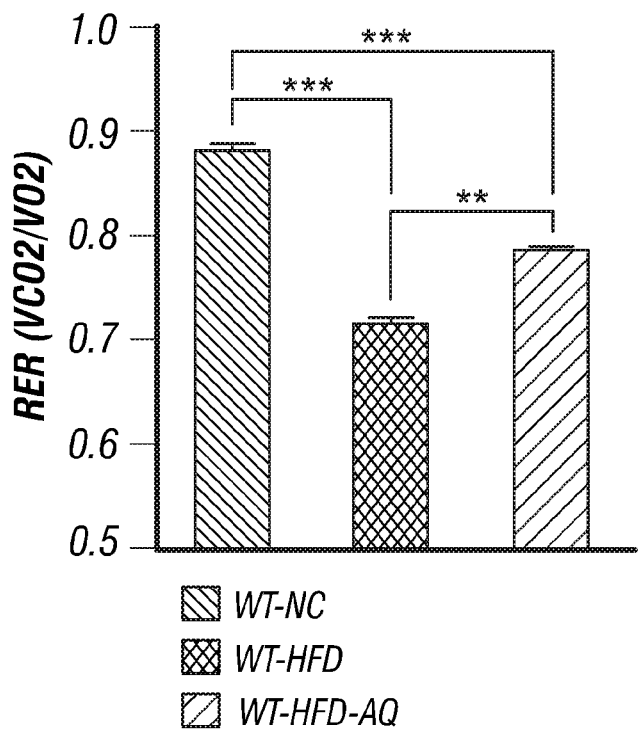
Figure 8A:
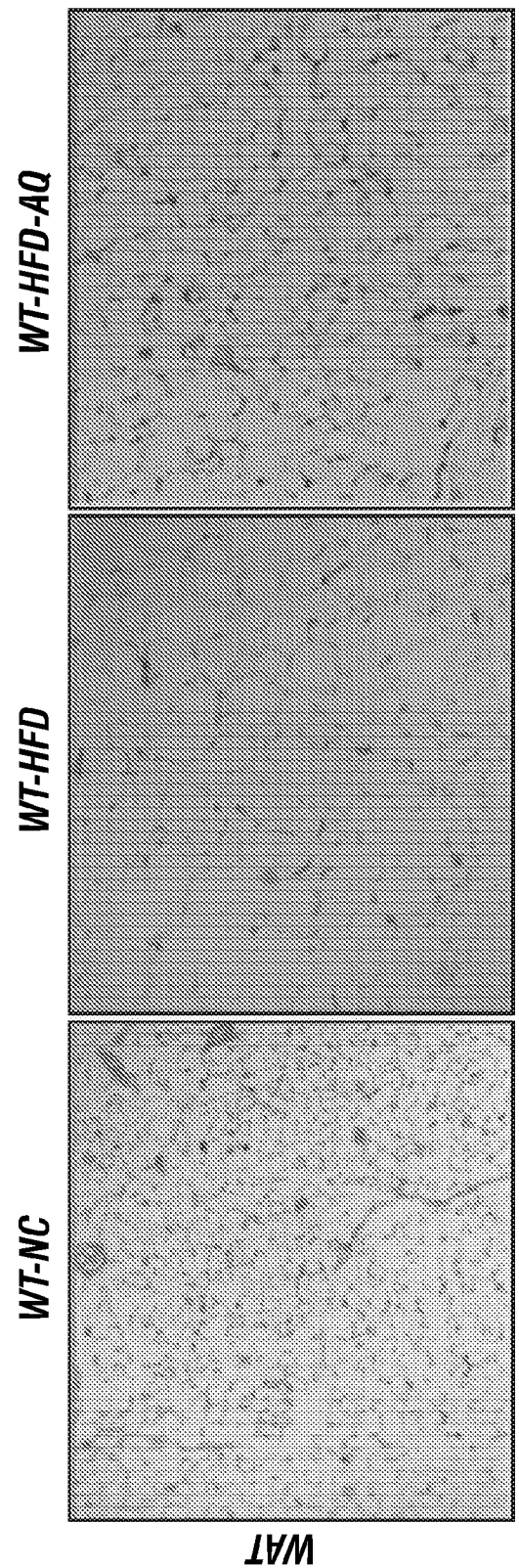
FIGS. 8A-B. AQ treatment decreases fat mass and adipocyte size.
Figure 8B:
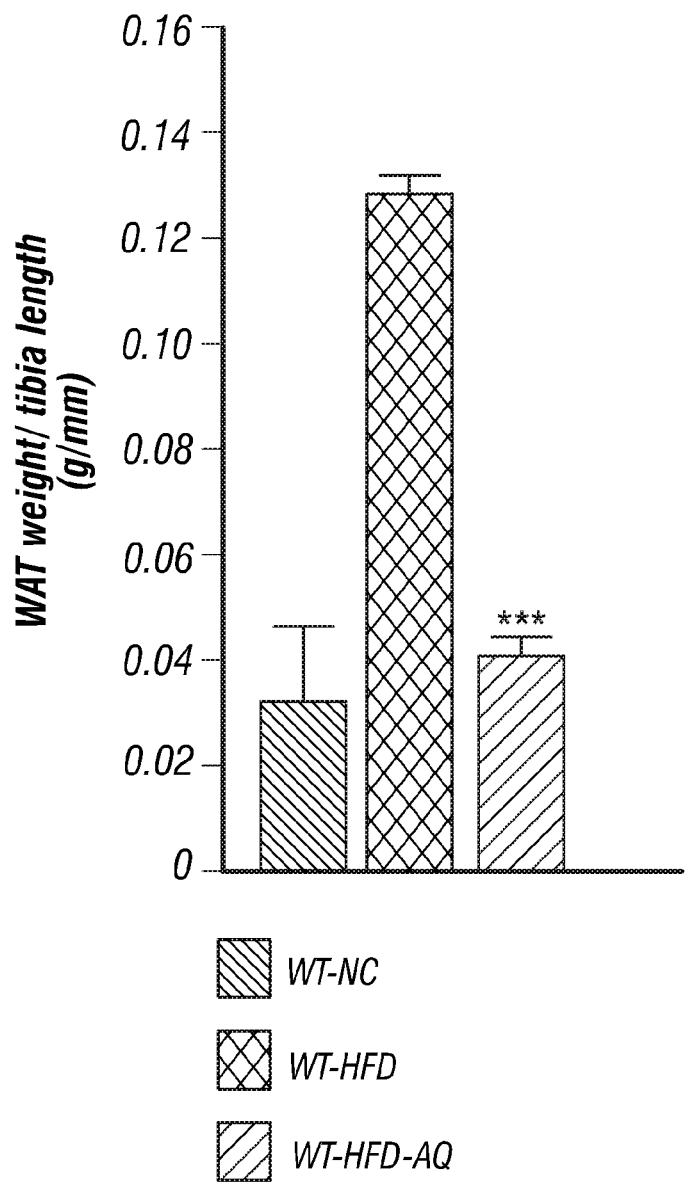

A putative Nurr1 agonist enhances metabolism and prevents hepatic steatosis. Nurr1 has been reported to be specifically activated by three cyclic compounds sharing a 4-amino-7-chloroquinoline scaffold. Among these compounds, amodiaquine (AQ) showed the highest activation levels. AQ drug is orally available drug and well tolerated in mice without adverse effects. The inventors therefore provided AQ to WT adult mice in the drinking water ad libitum maintained on normal chow (referred as WT-NC-CTL and WT-NC-AQ) and HFD (referred as WT-HFD-CTL and WT-HFD-AQ) for 10 weeks (FIG. 4A). When mice were maintained on normal chow, AQ had no effect on weight gain. However, when mice were maintained on HFD, AQ completely prevented obesity on HFD. Mice provided with AQ while on HFD showed body weights comparable to mice on normal chow, despite no difference in food consumption compared to control mice on HFD (FIGS. 4B-C). Moreover, WT-HFD-AQ mice show a significant decrease in fat mass and increase in lean mass composition compared to WT-HFD mice (FIG. 4D). The decrease in fat mass is correlated with a decrease in adipocyte size in white adipose tissue from WT-HFD-AQ compared to WT-HFD mice (FIGS. 8A-B). Additionally, AQ triggered a dramatic improvement in glucose and insulin tolerance of mice on HFD (FIGS. 4E-F). Serum insulin and triglyceride levels of WT-HFD-AQ mice were significantly lower than in WT-HFD mice (FIGS. 4G-H). To determine if the decrease in fat mass and improved glucose tolerance are shadowed by changes in energy expenditure, the inventors used metabolic cages to monitor the mice on NC and HFD. WT-HFD-AQ mice showed a significant increase in $O_2$ consumption, $CO_2$ production and RER compared to WT mice (FIGS. 4I-K).

Figure 4L:
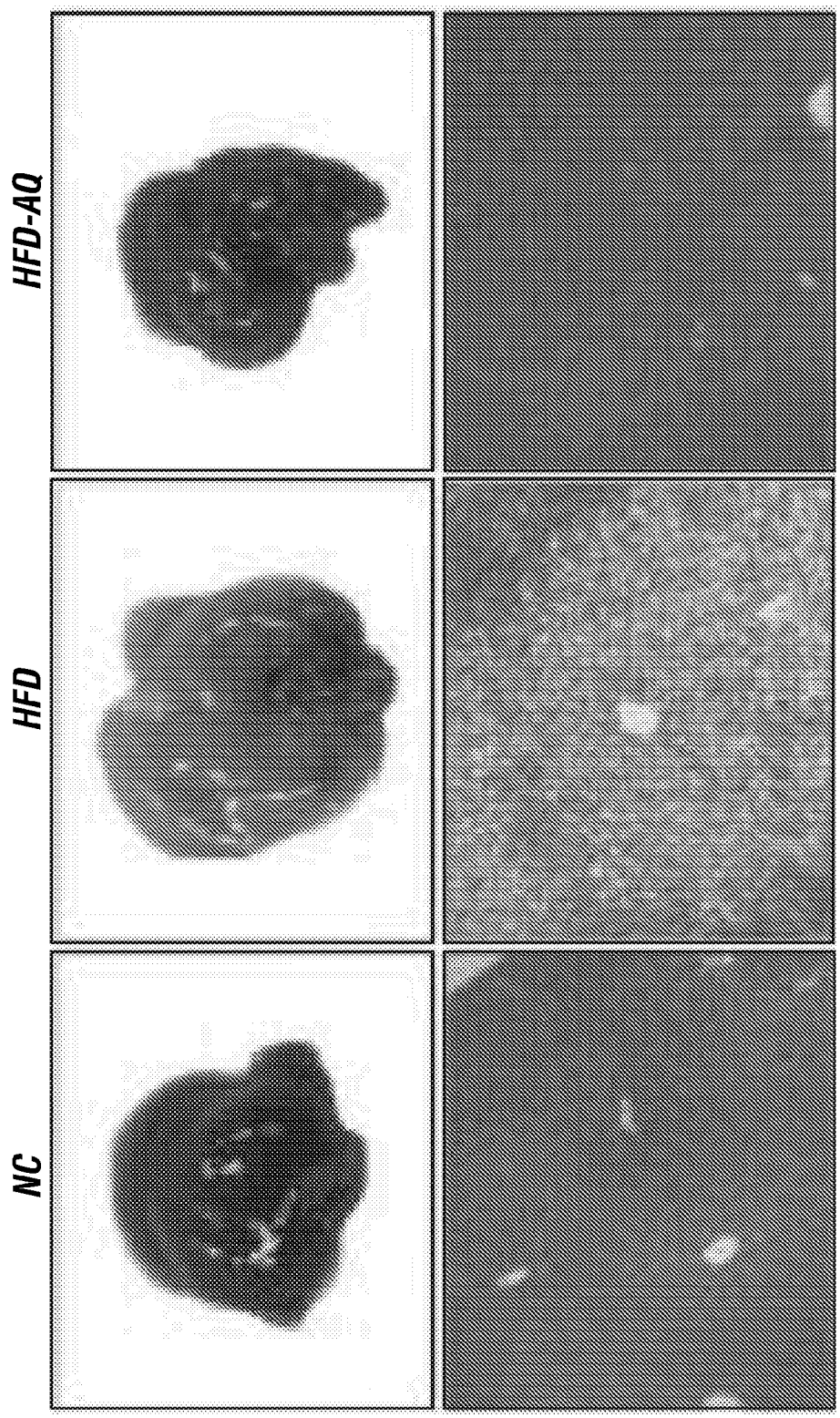
Figure 4M:
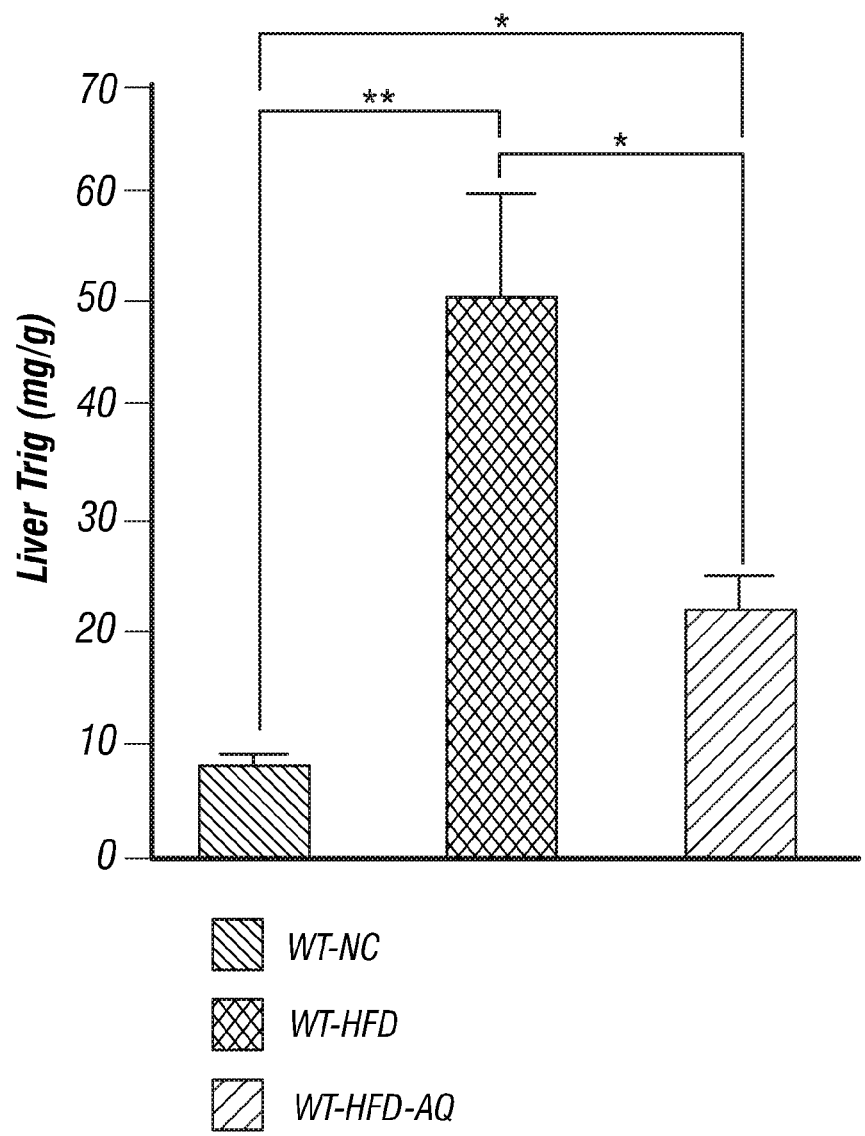

To investigate if Nurr1 agonist has an impact on hepatic steatosis expansion, the inventors looked at liver TRIG accumulation in response to HFD. As expected, after 8 weeks of HFD histological and biochemical analysis showed that WT mice develop hepatic steatosis with TRIG accumulation (FIG. 4L). However, the WT-HFD-AQ mice are resistant to the hepatic steatosis with a 50% decrease in hepatic TRIG levels (FIG. 4M). Taken together, these results show that Nurr1 agonist treatment prevents the development of HFD-induced obesity and associated metabolic disorders such as hyperglycemia, hyperinsulinemia and hepatic steatosis.

Nurr1 agonist enhances metabolism and reverts hepatic steatosis in obese mouse models. These results suggest that AQ treatment prevents the development of HFD-induced obesity. To determine if AQ can recover the metabolic disease in an obese model, the inventors used leptin deficient (ob/ob) mice. They then provided AQ to ob/ob adult mice in the drinking water ad libitum maintained on normal chow (referred as ob/ob-CTL and ob/ob-AQ) and compared to WT mice on normal chow (referred as WT-NC) for 4 weeks. At the start of the experiment ob/ob mice on normal chow weight 25% more then WT mice (referred as WT-NC-CTL). The ob/ob mice treated with AQ for 4 weeks lose weight and are resistant to weight gain despite consuming comparable quantities of chow (FIGS. 5A-D). Alongside with increased adiposity, ob/ob mice develop hepatic steatosis. To determine if AQ improved the hepatic steatosis, the inventors looked at liver TRIG accumulation. Histological and biochemical analysis show significant decrease of TRIG accumulation with 66% decrease in Tg levels in ob/ob-mice treated with AQ compared to non treated mice (FIGS. 5E-F).

Figure 9A:
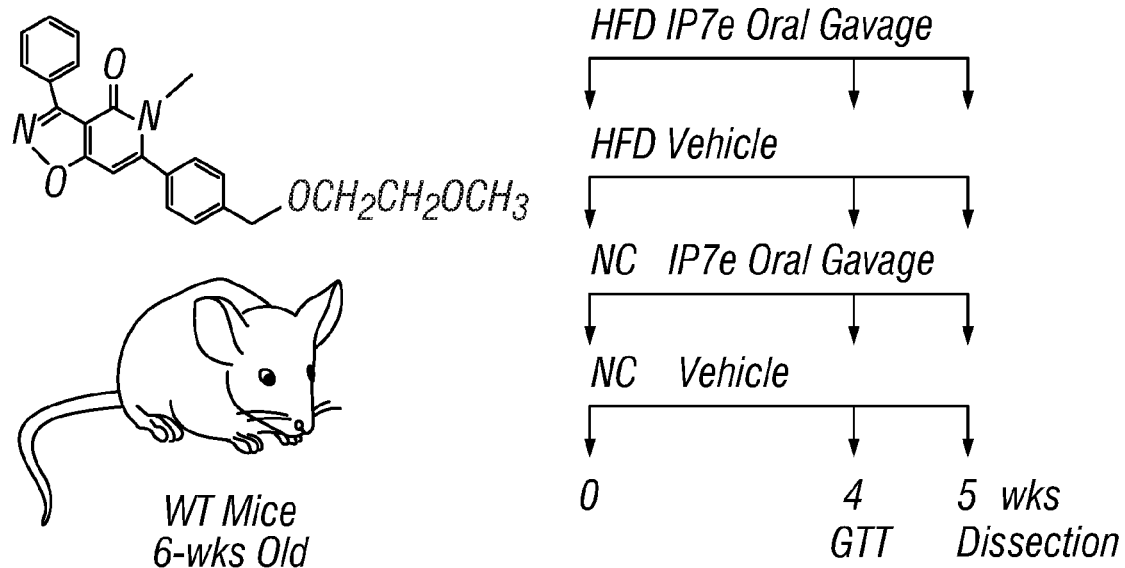
(FIG. 9A) Hematoxylin and eosin (H&E) of white adipose tissue (WAT).
Figure 9B:
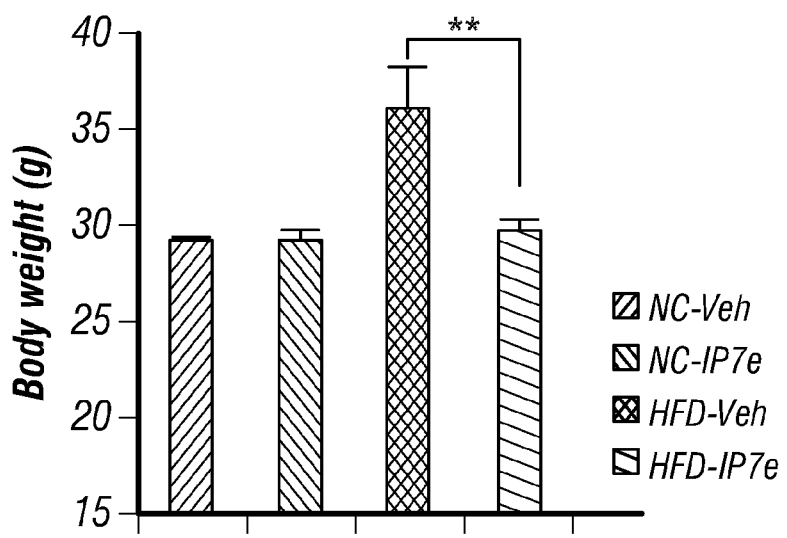
(FIG. 9B) WAT weights. Data are represented as mean±SEM. (n=8) ***P<0.0005.
Figure 9C:
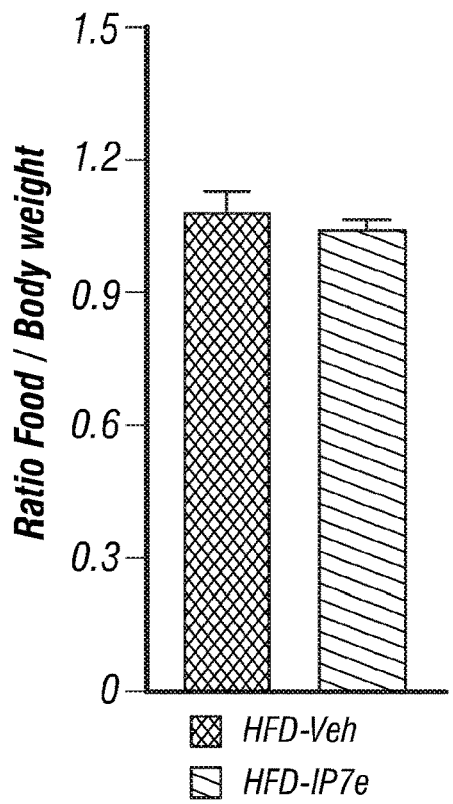
Figure 9D:
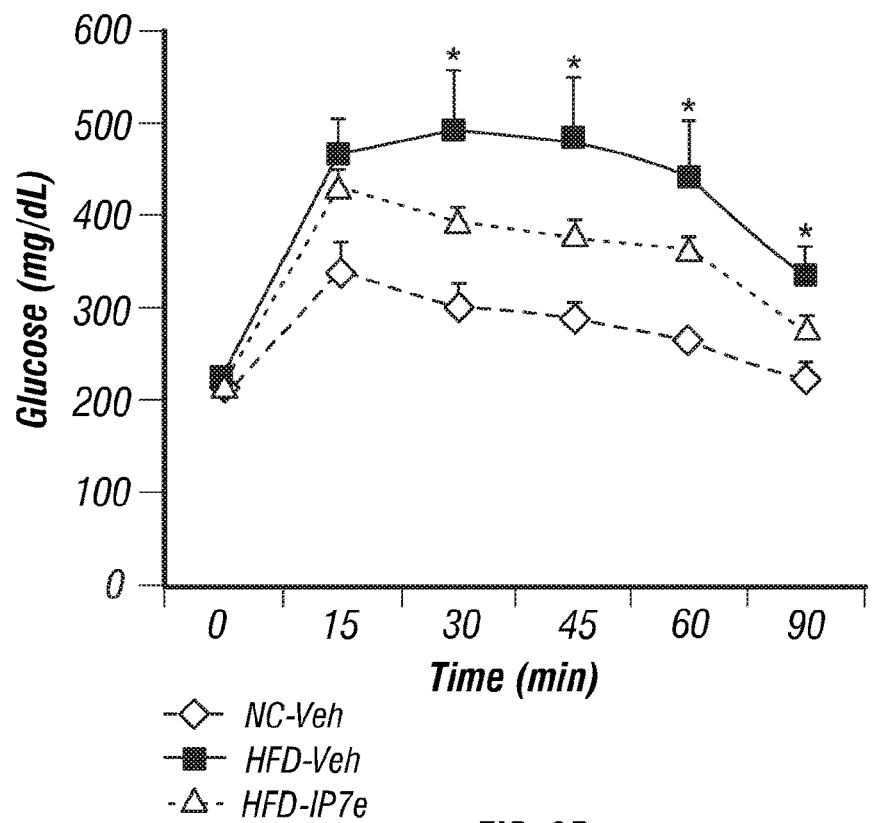

Nurr1 activation accounts for the beneficial metabolic effects of AQ. While AQ has been shown to act as a direct agonist of Nurr1 and these results show that AQ mimics certain of the metabolic actions of Nurr1 over-expression, this compound may also act through additional mechanisms. Therefore, the inventors compared its effects with a second Nurr1 agonist from a different chemical class. Isoxazolo-pyridinone 7e (iP7e) has been shown to activate Nurr1, but is structurally dissimilar to AQ. iP7e is a cell-permeable, isoxazolo-pyridinone compound that acts as a potent activator of Nurr1-dependent transcriptional activity. Then they provided iP7e to WT adult mice through oral gavage maintained on normal chow (referred as WT-NC-CTL and WT-NC-IP7e) and HFD (referred as WT-HFD-CTL and WT-HFD-IP7e) for 5 weeks (FIG. 9A). When mice were maintained on normal chow, IP7e had no impact on weight gain. However, when mice were maintained on HFD, IP7e prevented obesity, despite no difference in food consumption compared to control mice on HFD (FIGS. 9B-C). Additionally, IP7e elicited an improvement in glucose handling of mice on HFD (FIG. 9D).

Figure 9E:
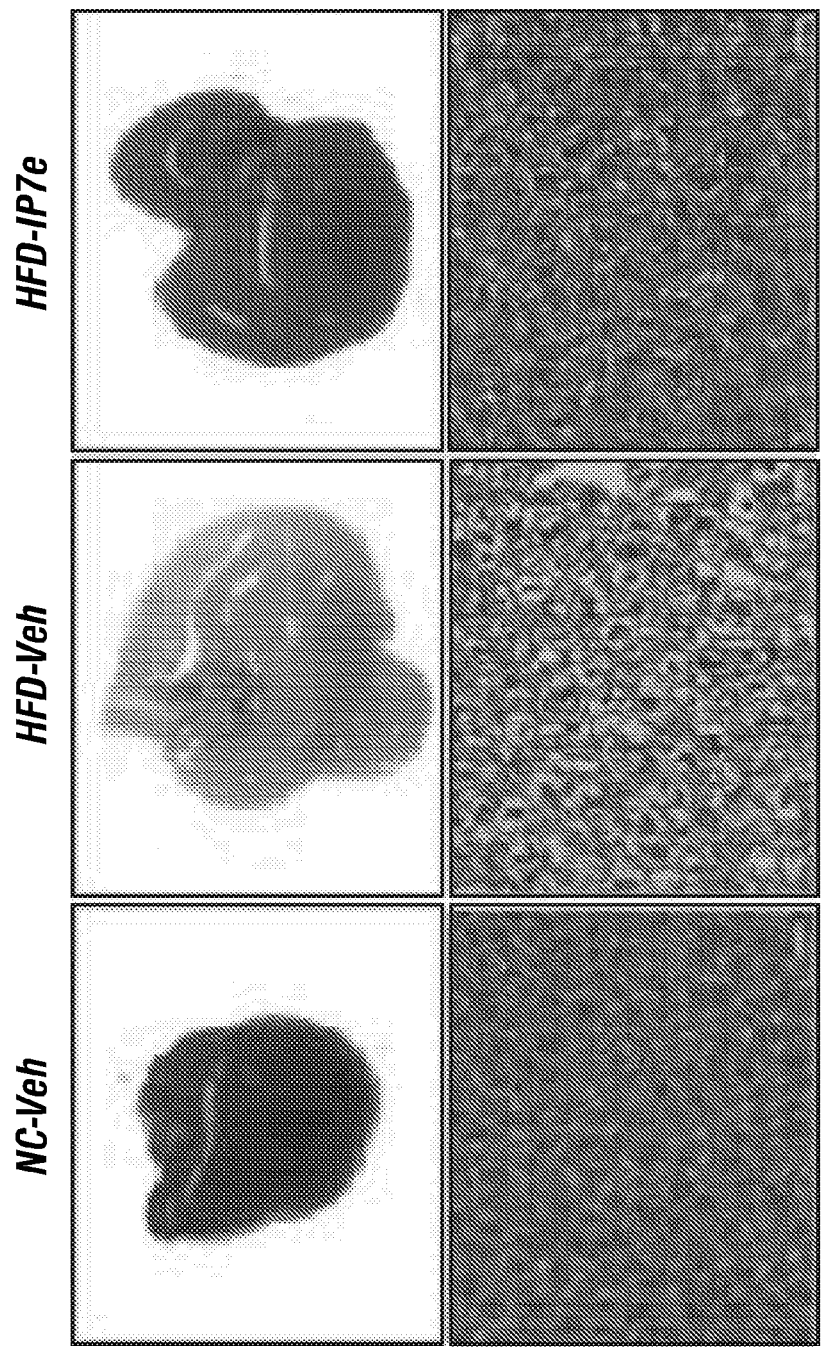
Figure 9F:
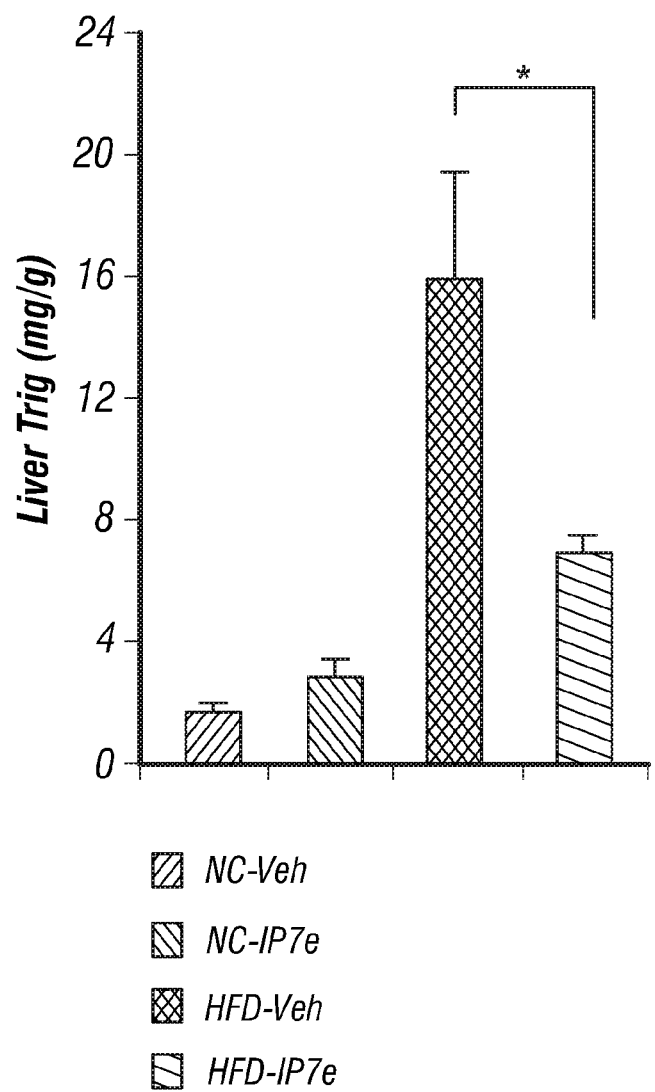

To examine if IP7e affected hepatic steatosis, the inventors looked at liver TRIG accumulation in response to HFD. Indeed, WT-HFD-IP7e mice were resistant to the hepatic steatosis with a 48% decrease in hepatic TRIG levels (FIGS. 9D-E). Thus, IP7e treatment prevents the development of HFD-induced obesity and associated metabolic disorders such as hyperglycemia and hepatic steatosis, mimicking the effects of AQ, and suggesting that Nurr1 activation evokes the metabolic beneficial actions observed in mice on HFD.

Example 3

Discussion

Figure 6:
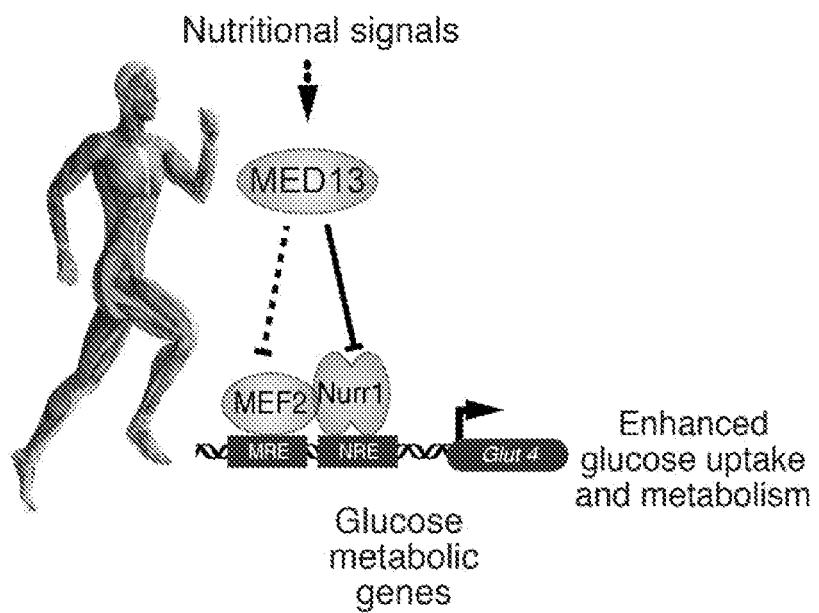
FIG. 6. A model of the role of skeletal muscle Nurr1 in the control of systemic metabolism. Nutritional stimuli regulate MED13 repressive function of NURR1. MED13 represses expression and activity of NURR1, which acts together with MEF2 as an activator of Glut4. Increased NURR1 muscle expression augments Glut4 expression and glycogen storage in skeletal muscle generating an insulin sensitizing effect, which is sensed primarily by the liver. Overexpression of Nurr1 in skeletal muscle confers an endurance phenotype. NURR1 agonist treatment confers a lean phenotype, mimicking the effects of exercise.

Despite extensive studies over several decades, the molecular basis of the benefits of exercise have not yet been fully elucidated. The results of this study reveal the components of a previously unrecognized gene regulatory program for the control of glucose uptake and utilization by skeletal muscle and a potential key to understanding the molecular underpinnings of the metabolic effects of exercise. Up-regulation of Nurr1 in response to MED13 deletion or transgenic over-expression confers a beneficial metabolic phenotype in mice, normalizing glucose and insulin levels under conditions of caloric excess and preventing hepatic steatosis. The ability of the putative Nurr1 agonist, AQ, to mimic the beneficial metabolic effects of Nurr1 up-regulation raises interesting possibilities with respect to pharmacologic manipulation of metabolic syndrome. Together with prior studies, these results support a model as shown in FIG. 6 for the transcriptional control of glucose metabolism in muscle and the consequent influence on systemic energy homeostasis.

Nurr1 as a potential mediator of exercise. Nurr1 has been identified as one of the most up-regulated gene in human skeletal muscle in response to exercise (Catoire et al., 2012). Expression of Nurr1 in skeletal muscle has also been shown to decline in mice exposed to HFD (Fu et al., 2007). Changes in expression of Nurr1 and the related orphan nuclear receptors, NR4A1 (Nur77) and NR4A3 (Nor1), have also been associated with alterations in lipid, carbohydrate and energy homeostasis in mice (Pearen et al., 2012; Chao et al., 2007). However, the potential causal role of Nurr1 in the control of energy homeostasis and hepatic steatosis in vivo has not been previously explored.

The metabolic effects of AQ. AQ and related compounds sharing a 4-amino-7-chloroquinoline scaffold are well known antimalarial drugs and have also been shown to display neuroprotective activity by protecting dopaminergic neurons from injury by environmental toxins and microglia-dependent neuroinflammation (Kim et al., 2015). These compounds have also been shown to regulate autophagy. However, beneficial metabolic effects of these compounds have not, to the inventors' knowledge, been reported.

AQ and similar compounds have been shown to interact with the ligand-binding domain of Nurr1, enhancing transcriptional activity. While these findings are consistent with Nurr1 agonism in skeletal muscle as the molecular basis for the beneficial metabolic effects of AQ, it is conceivable that AQ exerts its systemic metabolic effects by acting on tissues other than or in addition to skeletal muscle (e.g., adipose or the CNS). The inventors also have not ruled out the possibility that AQ might act through Nurr1-independent mechanisms. In this regard, the inventors note that AQ prevents weight gain in normal mice on HFD and in ob/ob mice, whereas transgenic over-expression of Nurr1 in skeletal muscle does not cause weight reduction. Despite these uncertainties, the remarkable metabolic actions of AQ suggest the potential benefits of this class of compounds in a variety of metabolic disorders. The inventors have observed no toxic effects of AQ in mice, supporting the conclusion that the suppressive actions of the drug on weight gain represent a physiologic mechanism rather than toxicity.

Millions of people have been treated with chloroquine, same class compound, as an anti-malarial drug. Three clinical observational studies showed that patients with autoimmune inflammatory arthritis treated with hydroxy-chloroquine, a 4-amino-7-chloroquinoline scaffold compound, had a lower risk of developing diabetes. In addition, two clinical trials reported that treatment with hydroxy-chloroquine in high doses lowers glucose level in individuals with type 2 diabetes and without autoimmune conditions. However, the mechanisms by which hydroxy-chloroquine may affect blood glucose and reduce the risk for type 2 diabetes has not been established. In this study, the inventors show for first time that Nurr1 AQ agonist prevents the development of metabolic disorders associated with obesity. Moreover, these findings suggest that AQ treatment in obese models restore hepatic steatosis and hyperinsulinemia to normal levels.

A transcriptional pathway for muscle metabolism. Previously, the inventors showed that chronic exercise stimulates the activity of the MEF2 transcription factor, which directly regulates the expression of GLUT4 and other metabolic genes. In addition, MEF2 activates expression of PGC-1 and serves as a coactivator of PGC-1 to enhance metabolism. Exercise enhances MEF2 activity through activation of calcium-dependent kinases that phosphorylate class II HDACs, promoting their export from the nucleus and derepression of MEF2. In addition, genetic deletion of MED13 enhances MEF2 activity, at least in part through up-regulation of SIK-1, a class II HDAC kinase.

Skeletal muscle displays a range of fiber types with distinctive metabolic and contractile properties. Type I myofibers, which display a slow contractile phenotype, as associated with improved metabolic function. MEF2 drives the slow myofiber gene program. However, in Nurr1 transgenic mice or mice treated with AQ, the inventors did not observe an increase in slow myofiber number. Thus, the beneficial metabolic actions of Nurr1 expression or treatment with AQ appear to reflect more direct action on the expression of GLUT4, etc.

Numerous myokines secreted by skeletal muscle in response to exercise have been shown to act on adipose and liver to modulate metabolism. However, these results show that MED13 and Nurr1 regulate systemic energy homeostasis independently of myokines through their regulation of GLUT4 expression.

Looking to the future. The Mediator complex is comprised of at least 20 subunits, which are expressed in all cells and are thought to regulate general transcription through RNA Polymerase II. Thus, it is intriguing that numerous mediator subunits have been implicated in metabolic control. In the future, it will be of interest to determine whether other meditator components act in skeletal muscle to control the activity or expression of Nurr1 and thereby modulate systemic energy homeostasis. Given the growing prevalence of hepatic steatosis as a consequence of obesity and metabolic syndrome, these findings highlight an unexplored mechanism for counteracting this pathological response to caloric excess.

Although the present disclosure and its advantages have been described in detail, it should be understood that various changes, substitutions and alterations can be made herein without departing from the disclosure as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

V. REFERENCES

The following references, to the extent that they provide exemplary procedural or other details supplementary to those set forth herein, are specifically incorporated herein by reference.

Amoasii, L., Holland, W., Sanchez-Ortiz, E., Baskin, K. K., Pearson, M., Burgess, S. C., Nelson, B. R., Bassel-Duby, R., and Olson, E. N. (2016). A MED13-dependent skeletal muscle gene program controls systemic glucose homeostasis and hepatic metabolism. Genes Dev. 30, 434-446.

Catoire, M., Mensink, M., Boekschoten, M. V., Hangelbroek, R., Müller, M., Schrauwen, P., and Kersten, S. (2012). Pronounced effects of acute endurance exercise on gene expression in resting and exercising human skeletal muscle. PLoS ONE 7, e51066.

Chao, L. C., Zhang, Z., Pei, L., Saito, T., Tontonoz, P., and Pilch, P. F. (2007). Nur77 coordinately regulates expression of genes linked to glucose metabolism in skeletal muscle. Mol. Endocrinol. 21, 2152-2163.

De Miranda et al. (2015a). Novel para-phenyl substituted diindolylmethanes protect against MPTP neurotoxicity and suppress glial activation in a mouse model of Parkinson's disease.Toxicol Sci. 143(2):360-73.

De Miranda et al. (2015b). The Nurr1 Activator 1,1-Bis(3'-Indolyl)-1-(p-Chlorophenyl)Methane Blocks Inflammatory Gene Expression in BV-2 Microglial Cells by Inhibiting Nuclear Factor κB. Mol Pharmacol. 87(6):1021-34.

Fu, Y., Luo, L., Luo, N., Zhu, X., and Garvey, W. T. (2007). NR4A orphan nuclear receptors modulate insulin action and the glucose transport system: potential role in insulin resistance. J. Biol. Chem. 282, 31525-31533.

Grueter, C. E., van Rooij, E., Johnson, B. A., DeLeon, S. M., Sutherland, L. B., Qi, X., Gautron, L., Elmquist, J. K., Bassel-Duby, R., and Olson, E. N. (2012). A cardiac microRNA governs systemic energy homeostasis by regulation of MED13. Cell 149, 671-683.

Kim, C.-H., Han, B.-S., Moon, J., Kim, D.-J., Shin, J., Rajan, S., Nguyen, Q. T., Sohn, M., Kim, W.-G., Han, M., et al. (2015). Nuclear receptor Nurr1 agonists enhance its dual functions and improve behavioral deficits in an animal model of Parkinson's disease. Proc. Natl. Acad. Sci. U.S.A. 112, 8756-8761.

Lin, J., Wu, H., Tarr, P. T., Zhang, C.-Y., Wu, Z., Boss, O., Michael, L. F., Puigserver, P., Isotani, E., Olson, E. N., et al. (2002). Transcriptional co-activator PGC-1 alpha drives the formation of slow-twitch muscle fibres. Nature 418, 797-801.

M Lehnen, A. (2013). Changes in the GLUT4 Expression by Acute Exercise, Exercise Training and Detraining in Experimental Models. J Diabetes Metab 01.

McKinsey, T. A., Zhang, C. L., and Olson, E. N. (2000). Activation of the myocyte enhancer factor-2 transcription factor by calcium/calmodulin-dependent protein kinase-stimulated binding of 14-3-3 to histone deacetylase 5. Proc. Natl. Acad. Sci. U.S.A. 97, 14400-14405.

Montarolo, F., Raffaele, C., Perga, S., Martire, S., Finardi, A., Furlan, R., et al. (2014). Effects of Isoxazolo-Pyridinone 7e, a Potent Activator of the Nurr1 Signaling Pathway, on Experimental Autoimmune Encephalomyelitis in Mice. PLoS ONE, 9(9), e108791.

Pearen, M. A., Eriksson, N. A., Fitzsimmons, R. L., Goode, J. M., Martel, N., Andrikopoulos, S., and Muscat, G. E. O. (2012). The Nuclear Receptor, Nor-1, Markedly Increases Type II Oxidative Muscle Fibers and Resistance to Fatigue. Mol. Endocrinol. 26, 372-384.

Potthoff, M. J., and Olson, E. N. (2007). MEF2: a central regulator of diverse developmental programs. Development 134, 4131-4140.

Richter, E. A., and Hargreaves, M. (2013). Exercise, GLUT4, and Skeletal Muscle Glucose Uptake. Physiological Reviews 93, 993-1017.

What is claimed:

1. A method of inducing weight loss in a subject that is obese comprising administering to said subject a bis (3'-indolyl)-containing molecule.

2. The method of claim 1, wherein said bis (3'-indolyl)-containing molecule is amodiaquine or a derivative or analog thereof.

3. The method of claim 1, further comprising providing a second agent that normalizes metabolism.

4. The method of claim 3, wherein said second agent is an anti-inflammatory agent, insulin or leptin.

* * * * *